(12) United States Patent
Schvalb et al.

(10) Patent No.: US 9,039,057 B2
(45) Date of Patent: May 26, 2015

(54) ORIENTATION CONTROLLER, MECHANICAL ARM, GRIPPER AND COMPONENTS THEREOF

(75) Inventors: Nir Schvalb, Nesher (IL); Boaz Ben Moshe, Herzlia (IL); Alon Vardimon, Beer-Sheva (IL); Barak Shamur, Petach-Tikva (IL)

(73) Assignee: Ariel-University Research and Development Company Ltd., Ariel (IL)

( * ) Notice: Subject to any disclaimer, the term of this patent is extended or adjusted under 35 U.S.C. 154(b) by 262 days.

(21) Appl. No.: 13/497,296

(22) PCT Filed: Sep. 21, 2010

(86) PCT No.: PCT/IB2010/054267
§ 371 (c)(1),
(2), (4) Date: Mar. 21, 2012

(87) PCT Pub. No.: WO2011/036626
PCT Pub. Date: Mar. 31, 2011

(65) Prior Publication Data
US 2012/0186383 A1 Jul. 26, 2012

Related U.S. Application Data

(60) Provisional application No. 61/244,455, filed on Sep. 22, 2009.

(51) Int. Cl.
*B25J 15/00* (2006.01)
*A61F 2/58* (2006.01)
(Continued)

(52) U.S. Cl.
CPC .............. *B25J 15/0009* (2013.01); *A61F 2/54* (2013.01); *A61F 2/586* (2013.01); *A61F 2/68* (2013.01); *A61F 2002/741* (2013.01); *B25J 9/104* (2013.01); *Y10S 901/31* (2013.01)

(58) Field of Classification Search
CPC ...... B25J 15/0009; B25J 9/1045; B25J 15/10; B25J 15/12; A61F 2/586; A61F 2/583; B66C 3/04; Y10S 901/31; Y10S 294/902
USPC ......... 294/106, 213, 111; 901/31, 39; 623/64; 403/145
See application file for complete search history.

(56) References Cited

U.S. PATENT DOCUMENTS

| | | |
|---|---|---|
| 1,423,296 A | 7/1922 | Armstrong |
| 1,466,163 A | 8/1923 | Harris |

(Continued)

FOREIGN PATENT DOCUMENTS

| | | |
|---|---|---|
| CN | 101214659 | 7/2008 |
| EP | 1195151 | 4/2002 |

(Continued)

OTHER PUBLICATIONS

Masters Thesis entitled "Design and Control of an Anthropomorphic Robot Finger with Multi-point Tactile Sensation" May 2001.
(Continued)

*Primary Examiner* — Kaitlin Joerger
*Assistant Examiner* — Gabriela Puig

(57) ABSTRACT

A jointed mechanism including a segment coupled to a joint; and an elongated component coupled to the segment, where applying a pulling force to the elongated component rotates the segment around the joint, elastically deforming the elongated component; wherein the elastic deformation generates an elongated component elastic force sufficient to rotate the segment, in an opposite direction, in absence of the pulling force.

24 Claims, 18 Drawing Sheets

(51) Int. Cl.
*A61F 2/68* (2006.01)
*B25J 9/10* (2006.01)
*A61F 2/54* (2006.01)
*A61F 2/74* (2006.01)

(56) References Cited

U.S. PATENT DOCUMENTS

| | | | | |
|---|---|---|---|---|
| 2,542,316 | A | * | 2/1951 | Farrar, Jr. ............... 623/61 |
| 4,063,830 | A | * | 12/1977 | Ban .......................... 403/3 |
| 4,466,800 | A | | 8/1984 | Breiden |
| 4,685,924 | A | | 8/1987 | Massey |
| 4,865,376 | A | | 9/1989 | Leaver et al. |
| 4,921,293 | A | | 5/1990 | Ruoff et al. |
| 4,986,723 | A | | 1/1991 | Maeda |
| 4,998,763 | A | * | 3/1991 | Henke ................. 294/82.33 |
| 5,062,673 | A | * | 11/1991 | Mimura .................. 294/111 |
| 5,647,723 | A | * | 7/1997 | Rush ..................... 414/735 |
| 6,063,095 | A | | 5/2000 | Wang et al. |
| 6,171,316 | B1 | | 1/2001 | Kovac et al. |
| 6,244,644 | B1 | | 6/2001 | Lovchik et al. |
| RE38,335 | E | | 11/2003 | Aust et al. |
| 6,668,678 | B1 | | 12/2003 | Baba et al. |
| 6,851,951 | B2 | * | 2/2005 | Choi et al. ............. 434/262 |
| 6,896,704 | B1 | | 5/2005 | Higuchi et al. |
| 6,991,627 | B2 | | 1/2006 | Madhani et al. |
| 7,121,781 | B2 | | 10/2006 | Sanchez |
| 7,155,315 | B2 | | 12/2006 | Niemeyer et al. |
| 7,296,835 | B2 | * | 11/2007 | Blackwell et al. ......... 294/111 |
| 7,361,197 | B2 | * | 4/2008 | Winfrey .................. 623/64 |
| 7,594,912 | B2 | | 9/2009 | Cooper et al. |
| 8,052,185 | B2 | * | 11/2011 | Madhani ................. 294/106 |
| 8,177,856 | B2 | * | 5/2012 | Jaworski ................. 623/64 |
| 8,573,663 | B1 | * | 11/2013 | Lin et al. ................ 294/111 |
| 2006/0061146 | A1 | * | 3/2006 | Grace .................... 297/16.2 |
| 2006/0131908 | A1 | * | 6/2006 | Tadano ................... 294/111 |
| 2008/0319553 | A1 | * | 12/2008 | Puchhammer ............ 623/64 |
| 2011/0163561 | A1 | * | 7/2011 | Kim et al. .............. 294/111 |
| 2011/0230894 | A1 | | 9/2011 | Simaan et al. |
| 2012/0277762 | A1 | | 11/2012 | Lathrop et al. |
| 2013/0313844 | A1 | * | 11/2013 | De La Rosa Tames et al. ............ 294/106 |

FOREIGN PATENT DOCUMENTS

| | | |
|---|---|---|
| JP | 2005-349488 | 12/2005 |
| JP | 2005 349488 | 12/2005 |
| JP | 2006-255872 | 9/2006 |
| JP | 2006 255872 | 9/2006 |
| WO | WO 2005/009482 | 2/2005 |
| WO | WO 2011/036626 | 3/2011 |

OTHER PUBLICATIONS

De Laurentis K.J. et al "Rapid fabrication of a non-assembly robotic hand with embedded components" 2004, 24(4) 394-405.
Pisaturo, C. "Flexible Joint Robot Finger Jul. 2006" from www.carlpisaturo.com.
Notification of the Need to Submit Additional Materials Dated Jan. 27, 2014 From the Eurasian Patent Organization, The Eurasian Patent Office Re. Application No. 201290164 and Its Translation Into English.
International Preliminary Report on Patentability Dated Mar. 27, 2012 From the International Searching Authority Re. Application No. PCT/IB2010/054267.
International Search Report and the Written Opinion Dated May 24, 2011 From the International Searching Authority Re. Application No. PCT/IB2010/054267.
Office Action Dated Dec. 1, 2013 From the Israel Patent Office Re. Application No. 218107 and Its Translation Into English.
Office Action Dated Mar. 9, 2014 From the Israel Patent Office Re. Application No. 218107 and Its Translation Into English.
Banks "Design and Control of an Anthropomorphic Robotic Finger With Multi-Point Tactile Sensation", Massachussetts Institute of Technology, Artificial Intelligence Laboratory, AI Technical Report 2001-005, p. 1-88, May 2001.
De Laurentis et al. "Rapid Fabrication of a Non-Assembly Robotic Hand With Embedded Components", Assembly Automation, 24(4): 394-405, 2004.
Gomez et al. "An Adaptive Neural Controller for a Tendon Driven Robotic Hand", Intelligent Autonomous Systems, IOS Press, p. 1-10, 2003.
Pisaturo et al. "Flexible Joint Finger Jul. 2006", MIT Media lab, 2 P., 2006.
Communication Pursuant to Article 94(3) EPC Dated Jun. 11, 2014 From the European Patent Office Re. Application No. 10766120.9.
Communication Pursuant to Article 94(3) EPC Dated Nov. 4, 2014 From the European Patent Office Re. Application No. 10766120.9.

* cited by examiner

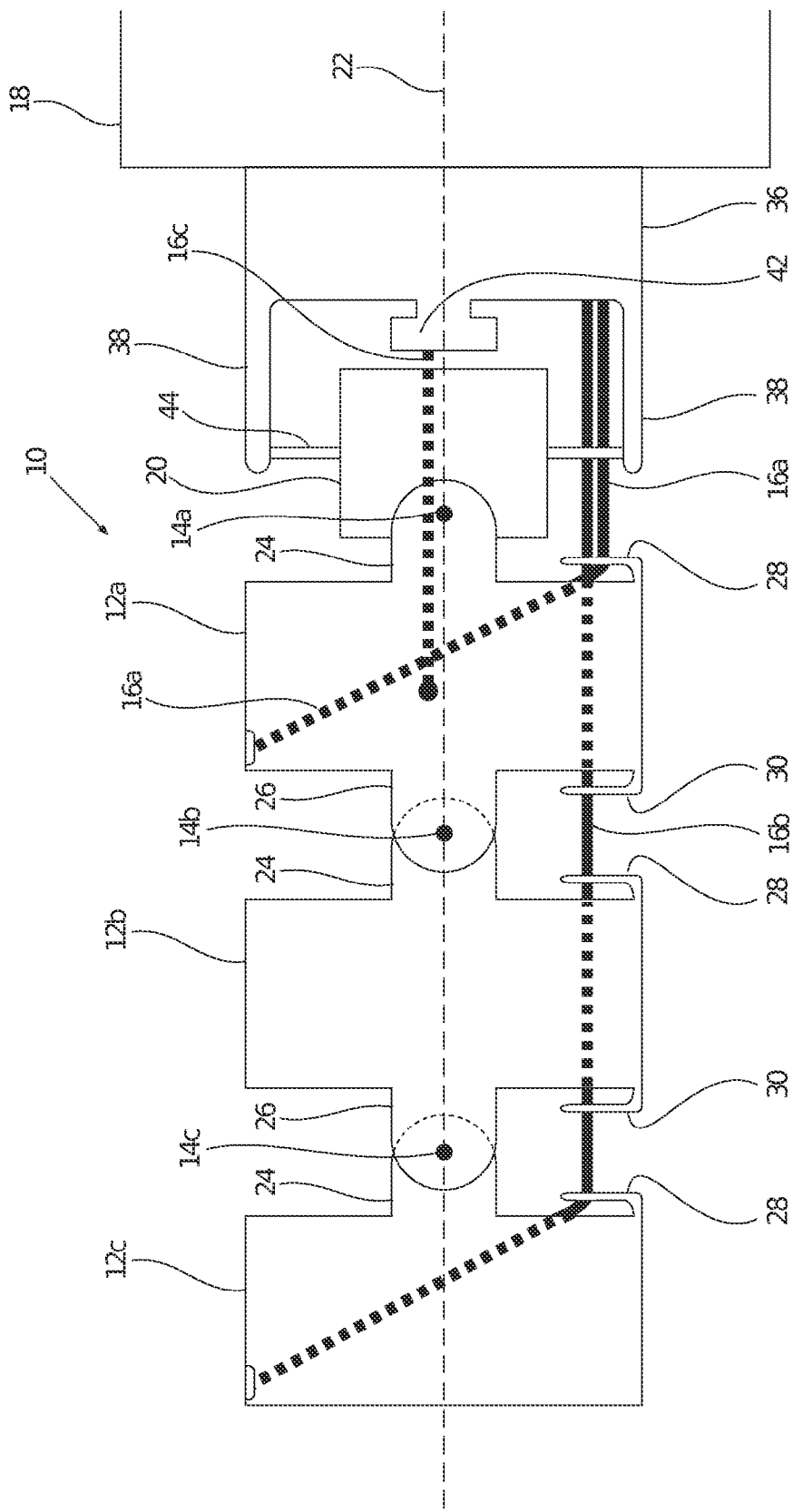

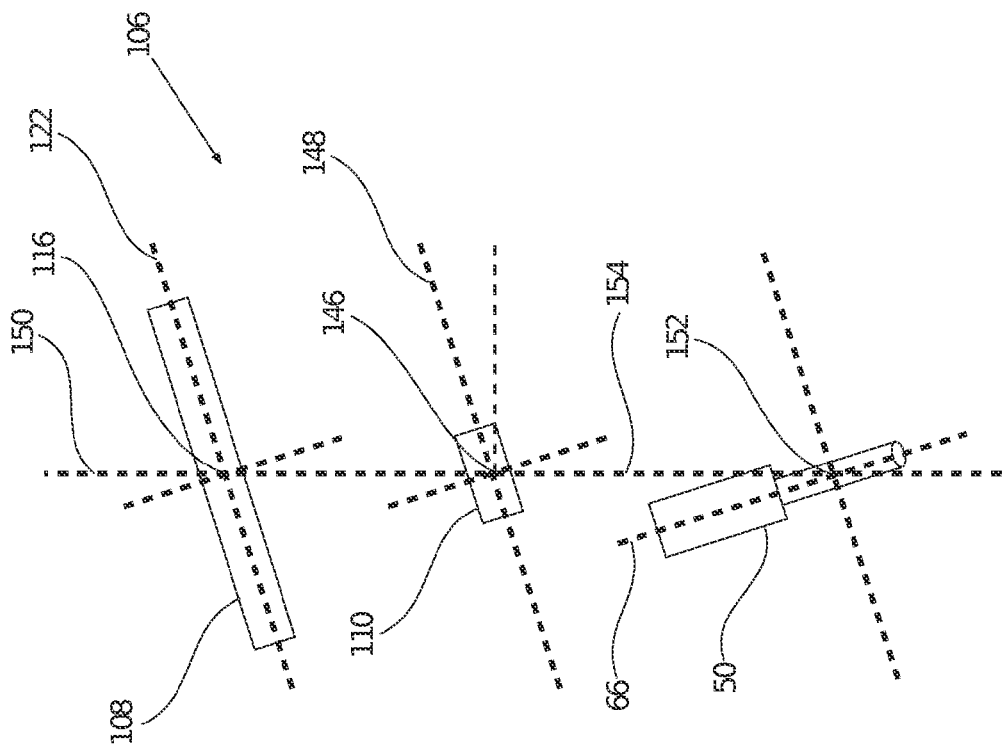
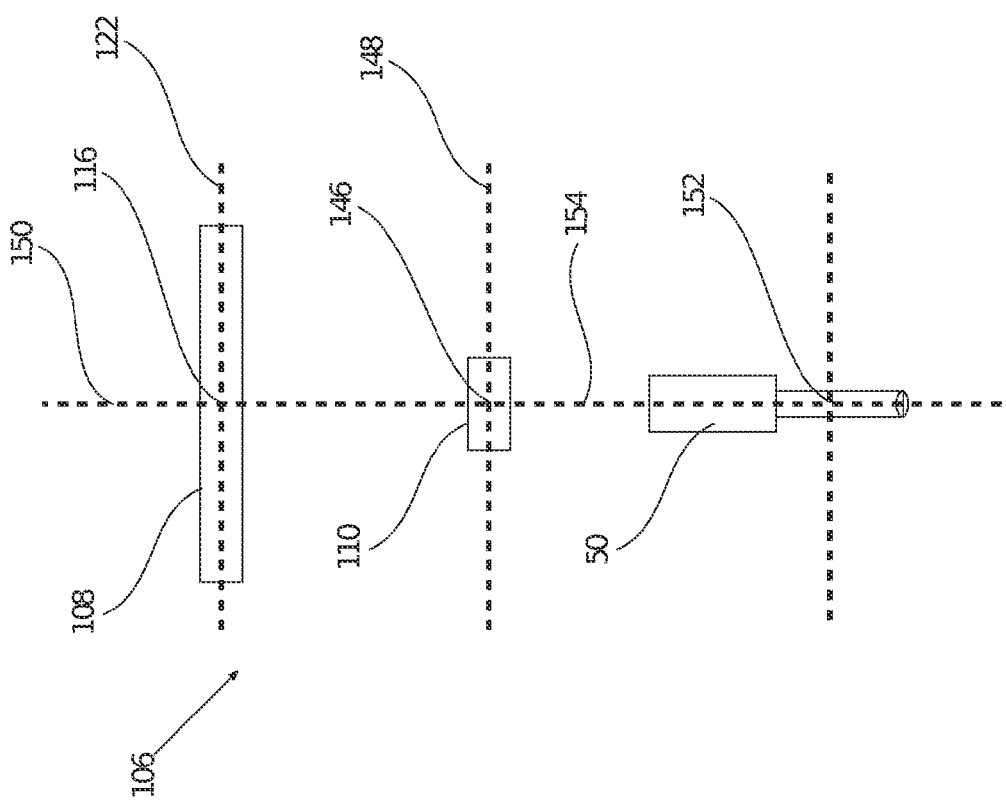
FIG. 6C
FIG. 6B

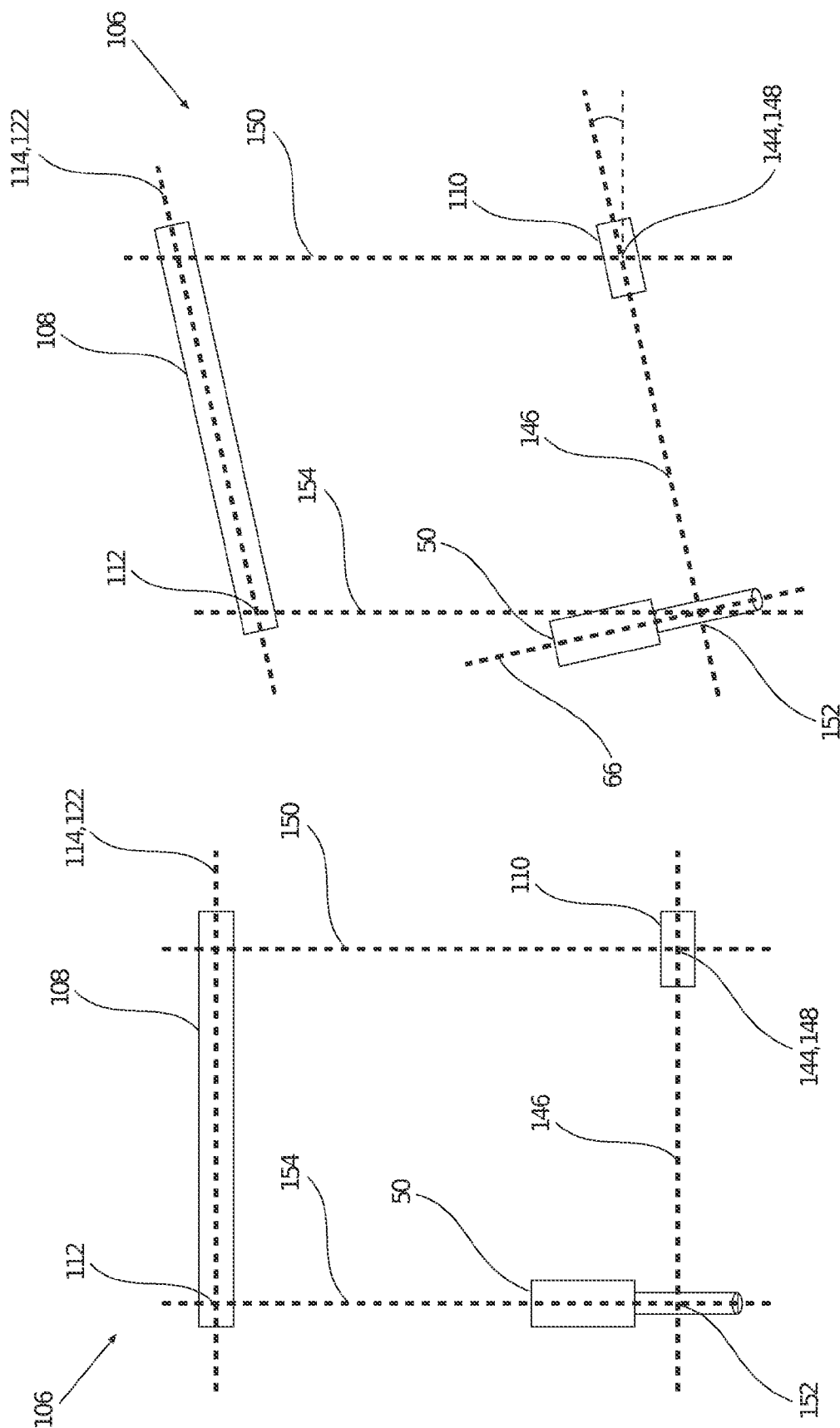

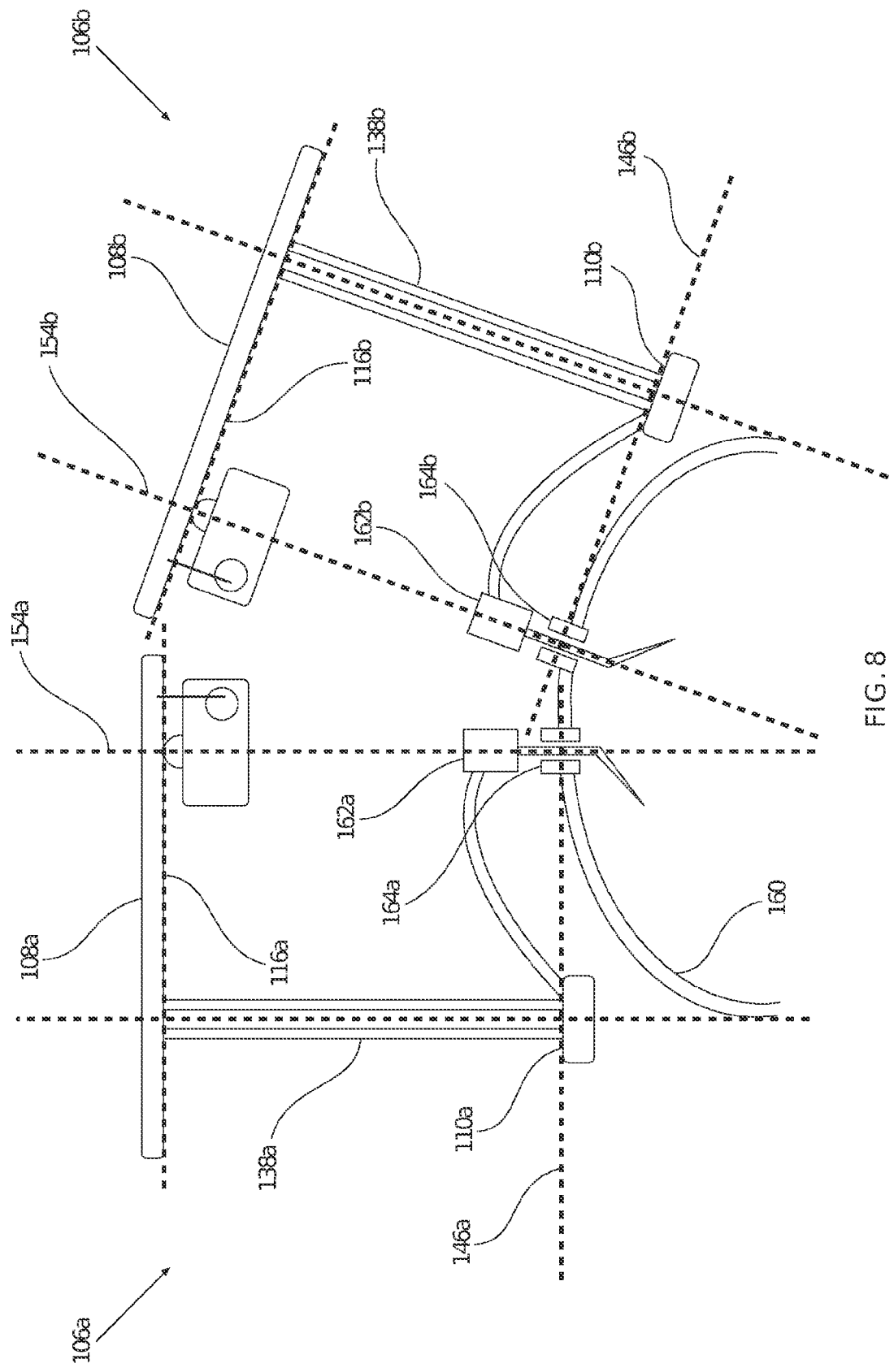

ORIENTATION CONTROLLER, MECHANICAL ARM, GRIPPER AND COMPONENTS THEREOF

RELATED APPLICATION

The present application gains priority from U.S. Provisional Patent Application No. 61/244,455 filed 22 Sep. 2009, and PCT Application PCT/IB2010/054267, filed 21 Sep. 2010 which are included by reference as if fully set forth herein.

FIELD AND BACKGROUND OF THE INVENTION

The invention, in some embodiments, relates to the field of mechanical grippers and manipulators and more particularly, but not exclusively, to anthropomorphic mechanical grippers. The invention, in some embodiments, relates to the field of keyhole surgery and more particularly, but not exclusively, to mechanical devices useful for performing keyhole surgery.

Anthropomorphic mechanical grippers that resemble human hands having at least two articulated digits that may be brought together to grasp an object are desirable.

Control of anthropomorphic grippers for human operation is exceptionally simple: an associated control system translates the hand motions of an operator, such as grasping, directly to motions of the gripper. For the operator the use of such a mechanical gripper is intuitive and easy to learn.

In the field of robots, robot-controlled anthropomorphic grippers are versatile and adaptable analogous to the hands of primates.

Anthropomorphic mechanical grippers have been described, for example, in U.S. Pat. Nos. 4,865,376; 4,921,293 and 6,244,644; Japanese patent application published as JP2006255872A, Chinese patent application CN 101214659A published as CN 200810056395; Banks J L (1994) *Design and control of an anthropomorphic robotic finger with multi-point tactile sensation*, MSc thesis at the Massachusetts Institute of Technology May 2001; Gómez G, Hernandez A, Eggenberger Hotz P, (2006) *An adaptive neural controller for a tendon driven robotic hand* in Proceedings of the 9th International Conference on Intelligent Autonomous Systems (IAS-9). T. Arai et al. (Eds.), IOS Press, Tokyo, Japan, pp. 298-307 as well as the works of Carl Pisaturo and of Gabriel Gómez (such as the Yokoi Robot Hands) described on the Internet.

A model of a human finger, suitable for use in education, has been described in U.S. Pat. No. 4,466,800.

Additional background art includes U.S. Pat. Nos. 6,312,435; 6,053,933; 5,456,684; 5,762,458; 3,990,321; 6,394,998; 5,797,900; 6,634,184; 7,367,772 and 5,792,135.

Anthropomorphic grippers are generally very complex assemblies comprising many small parts. Consequently, fabrication, assembly and repairs of such grippers are very expensive. Additionally, the ability to make small grippers is very limited.

SUMMARY OF THE INVENTION

Some aspects of the invention relate to anthropomorphic mechanical grippers, components thereof such as mechanical digits and methods of making the same that in some embodiments have advantages over known such mechanical grippers, for example in the field of keyhole surgery.

Aspects of the invention relate to a mechanical arm useful, for example, for controllably moving an end effector such as the mechanical gripper described herein, for example in the field of keyhole surgery.

Aspects of the invention relate to a mechanical orientation controller based on a parallelogram linkage useful, for example, for controlling the orientation of a tool such as a mechanical arm and/or an end effector such as a mechanical gripper as described herein, for example in the field of keyhole surgery.

According to an aspect of some embodiments of the invention there is provided, a mechanical digit, comprising:

a) a first hollow digit segment defining an axial void with an axis, a proximal end and a distal end;

b) a second hollow digit segment defining an axial void with an axis, a proximal end and a distal end, secured to the first digit segment with a first hinged joint (a joint that allows rotational motion in a single plane) so that the proximal end of the second digit segment faces the distal end of the first digit segment; and c) a tendon passing through the axial void of the first digit segment off (in some embodiments below) the axis of the first digit segment, entering the axial void of the second digit segment from the proximal end of the second digit segment and crossing a plane including the axis of the second digit segment inside the void to be secured to the second digit segment wherein the tendon is secured to the second digit segment so that:

pulling the tendon in a proximal direction causes downwards flexion (planar motion around the hinged decreasing the angle between the axis of the first digit segment and the axis of the second digit segment) of the digit relative to the axis around the first hinged joint; and subsequent to flexion, release of the tendon causes upward extension (planar motion around the hinged joint increasing the angle between the first digit segment and the second digit segment) of the digit. In some embodiments, the tendon is secured to the second digit segment above the axis of the second digit segment.

In some embodiments, the tendon is an elongated component elastic in a lateral direction, that is tends to spring back to an original position when released from an applied lateral force that bends the component. In some embodiments, the extension of the digit when the tendon is released is at least partially, and in some embodiments substantially entirely, a result of a force applied by the tendon.

In some embodiments, the digit further comprises a third digit segment defining an axial void with an axis, a proximal end and a distal end, secured to the first digit segment through a second hinged joint so that the proximal end of the first digit segment faces the distal end of the third digit segment, the tendon passing through the axial void of the third digit segment below the axis of the third digit segment and entering the axial void of the first digit segment from the proximal end of the first digit segment, wherein the pulling of the tendon in the proximal direction causes downwards flexion of the digit relative to the axis around the second hinged joint.

According to an aspect of some embodiments of the invention there is also provided, anthropomorphic gripper, comprising: a) a palm for supporting mechanical digits, the palm having a distal end and a proximal end; and b) at least two mechanical digits as described above, secured to the palm.

According to an aspect of some embodiments of the invention there is also provided a mechanical arm suitable for controllably moving an end effector secured thereto, comprising:

a) an arm support base having an arm axis;

b) a hollow support rod including an axial lumen parallel to the arm axis, fixedly secured to and extending distally from the arm support base;

c) a hollow extension unit including an axial lumen, secured to a distal end of the hollow support rod with a joint constituting a hinged elbow joint, where when the elbow joint is straight, the axial lumen of the hollow extension unit is substantially collinear with the axial lumen of the hollow support rod;

d) an upper rotating rod rotatably contained within the axial lumen of the hollow support rod having a distal end secured to a proximal end of a double cardan joint drive shaft substantially contained inside the elbow joint;

e) a lower rotating rod rotatably contained within the axial lumen of the hollow extension unit, a proximal end of the lower rotating rod secured to a distal end of the double cardan joint drive shaft, thereby rotatingly linking the lower rotating rod with the upper rotating rod through the double cardan joint drive shaft; and f) a wrist shell fixedly secured to a distal end of the lower rotating rod wherein axial rotation of a proximal end of the upper rotating rod leads to axial rotation of the lower rotating rod and the wrist shell substantially irrespective of an angle of the elbow joint.

An aspect of some embodiments of the invention is an orientation controller, based on a parallelogram linkage, that allows changing the angular orientation of an attached tool. According to an aspect of some embodiments of the invention there is also provided an orientation controller, comprising:

a) a base;

b) an orientation control linker defining a fixed longitudinal distance between a pivot point and an orientation transmission point, including a longitudinal axis between the pivot point and the orientation transmission point, the pivot point attached to the base through a joint allowing rotary motion relative to the base around the longitudinal axis and around a transverse axis perpendicular to the longitudinal axis;

c) extending from a proximity to the orientation transmission point in a substantially vertical direction, at least three rigid orientation transmission rods of substantially equal length, a proximal end of each orientation transmission rod linked to the orientation control linker through a joint allowing rotary motion relative to the orientation transmission point, wherein the proximal ends define a closed curve surrounding the orientation transmission point; and d) an orientation reception linker including an orientation reception point and a longitudinal axis parallel to the longitudinal axis of the orientation control linker, linked to a distal end of each orientation transmission rod through a joint allowing rotary motion relative to the orientation reception point, so that the orientation transmission rods are parallel.

In some embodiments, the components of the orientation controller constitute two orthogonal parallelogram linkages: a first parallelogram linkage functional for transferring transverse rotation of the orientation control linker to transverse rotation of the orientation reception linker comprising as vertices the pivot point, the orientation transmission point, the orientation reception point and a stationary point located at the intersection of the longitudinal axis of the orientation reception linker and a vertical axis passing through the pivot point and parallel to the orientation transmission rods; and a second parallelogram linkage functional for transferring longitudinal rotation of the orientation control linker to the orientation reception linker comprising as vertices the distal ends and the proximal ends of the orientation transmission rods located at a transverse dimension of the closed curve.

Unless otherwise defined, all technical and scientific terms used herein have the same meaning as commonly understood by one of ordinary skill in the art to which the invention pertains. In case of conflict, the specification, including definitions, will control.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, anthropomorphic terms such as "hand", "palm", "digit", "finger", "thumb", "finger tip", "joint", "tendon", "arm", "wrist", "elbow" and "shoulder" may be used for describing aspects and components of the devices described herein. Such terms are used in a non-limiting fashion, as known in the art of mechanical grippers and robotics, to ease understanding of the devices described herein. Specifically, "digit" is a general term that includes both "finger" and "thumb". "Thumb" refers to a digit that is opposable to other "digits" of a "hand".

BRIEF DESCRIPTION OF THE DRAWINGS

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIG. 1A is a schematic view of an embodiment of a mechanical digit as described herein;

FIGS. 6B-6C are schematic views of the rotation of the orientation controller of FIG. 6A around the longitudinal axis;

FIGS. 7B-7C are schematic views of the rotation of the orientation controller of FIG. 7A around the transverse axis;

FIG. 8 is a schematic view of an application of embodiments of an orientation controller as described herein, in which two embodiments of a orientation controller are used simultaneous to assist with keyhole surgery.

DESCRIPTION OF SOME EMBODIMENTS OF THE INVENTION

Figure 1B:
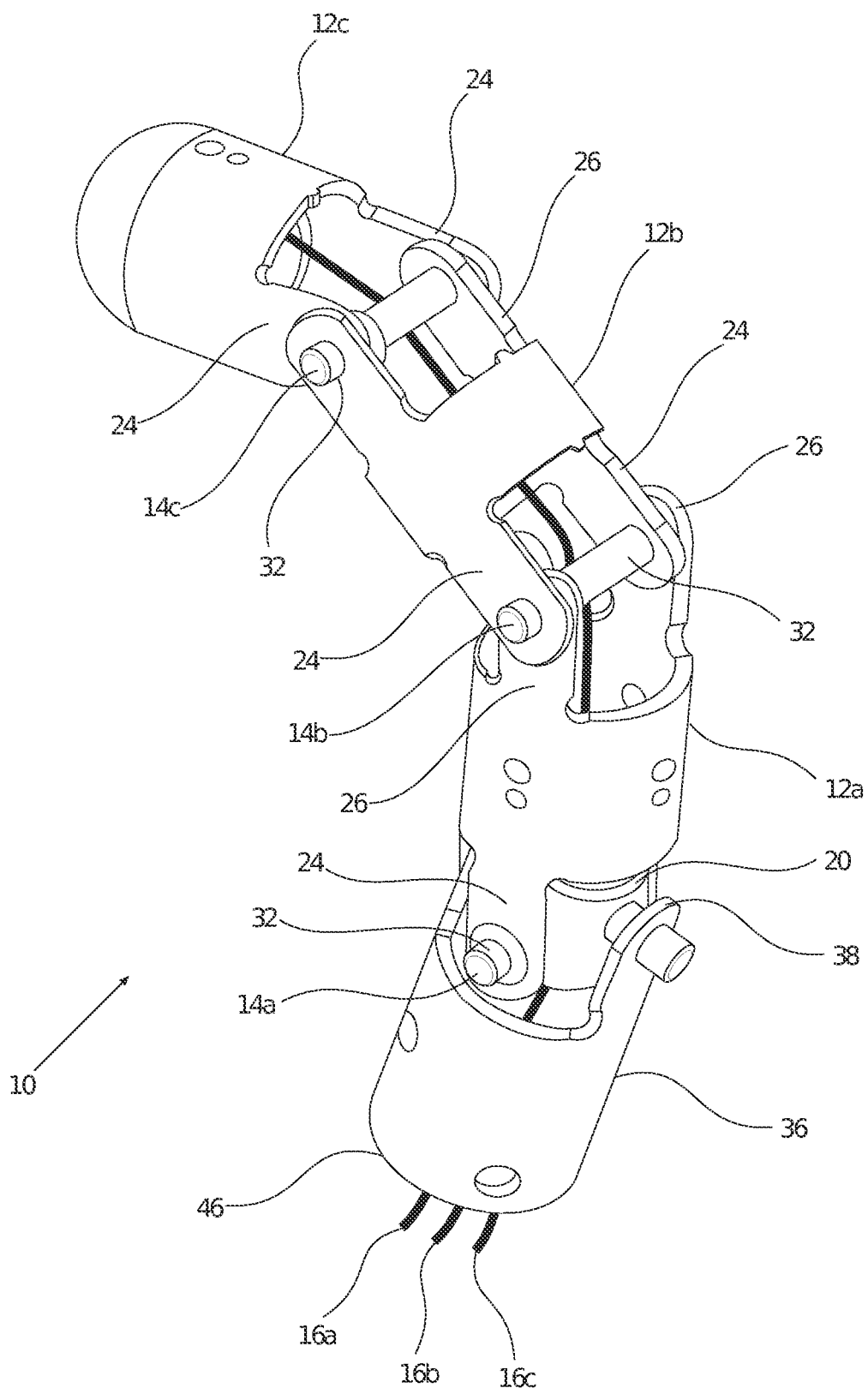
FIG. 1B is a perspective view of the mechanical digit of FIG. 1A.

The invention, in some embodiments thereof, relates to an anthropomorphic gripper, to mechanical digits useful, for example, for implementing an anthropomorphic gripper, and to a mechanical arm and orientation controller useful for manipulating, orienting and controlling an end effector or tool, for example the gripper described herein.

The principles, uses and implementations of the teachings of the invention may be better understood with reference to the accompanying description and figures. Upon perusal of the description and figures present herein, one skilled in the art is able to implement the teachings of the invention without undue effort or experimentation. In the figures, like reference numerals refer to like parts throughout.

Before explaining at least one embodiment of the invention in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.
Mechanical Digit An aspect of some embodiments of the invention is a mechanical digit that is useful in implementing an anthropomorphic gripper as described herein.

According to an aspect of some embodiments of the invention there is provided, a mechanical digit, comprising:

a) a first hollow digit segment defining an axial void with an axis, a proximal end and a distal end;

b) a second hollow digit segment defining an axial void with an axis, a proximal end and a distal end, secured to the first digit segment with a first hinged joint (a joint that allows rotational motion in a single plane) so that the proximal end of the second digit segment faces the distal end of the first digit segment; and c) a tendon passing through the axial void of the first digit segment below the axis of the first digit segment, entering the axial void of the second digit segment from the proximal end of the second digit segment and crossing the axis of the second digit segment inside the void to be secured to the second digit segment wherein the tendon is secured to the second digit segment so that:

pulling the tendon in a proximal direction causes downwards flexion (planar motion around the hinged decreasing the angle between the axis of the first digit segment and the axis of the second digit segment) of the digit relative to the axis around the first hinged joint; and subsequent to flexion, release of the tendon causes upward extension (planar motion around the hinged joint increasing the angle between the first digit segment and the second digit segment) of the digit.

In some embodiments, the tendon is secured to the second digit segment above the axis of the second digit segment.

In some embodiments, the tendon is an elongated component elastic in a lateral direction, that is tends to spring back to an original position when released from an applied lateral force that bends the component. Preferably, the tendon does not substantially lengthen when an axial stretching force is applied thereto. In some embodiments, the tendon is a wire. In a preferred embodiment the tendon is of a super-elastic material such as Nitinol.

In some embodiments, the extension of the digit when the tendon is released is at least partially, and in some embodiments substantially entirely, a result of a force applied by the tendon.

In some embodiments, the first digit segment includes at least one tendon guide to maintain the tendon below the axis when passing through the axial void of the first digit segment.

In some embodiments, the second digit segment includes at least one tendon guide to maintain the tendon below the axis when entering the axial void of the second digit segment through the proximal end thereof.

In some embodiments, the digit further comprises a third digit segment defining an axial void with an axis, a proximal end and a distal end, secured to the first digit segment through a second hinged joint so that the proximal end of the first digit segment faces the distal end of the third digit segment, the tendon passing through the axial void of the third digit segment below the axis of the third digit segment and entering the axial void of the first digit segment from the proximal end of the first digit segment, wherein the pulling of the tendon in the proximal direction causes downwards flexion of the digit relative to the axis around the second hinged joint.

In some embodiments, the downwards flexion of the second hinged joint is substantially coplanar with the downwards flexion of the first hinged joint.

In some embodiments, the third digit segment includes at least one tendon guide to maintain the tendon below the axis when passing through the axial void of the third digit segment.

Referring now to the schematic view of FIG. 1A and the perspective view of FIG. 1B, there is shown a schematic view of an embodiment of a mechanical digit 10 as described herein.

Digit 10 comprises three hollow digit segments 12a, 12b and 12c, three joints 14a, 14b and 14c and three tendons 16a, 16b and 16c. Digit 10 is attached to palm 18 through abduction adapter 20 and digit base 36. Joints 14 define digit axis 22 that is straight when digit 10 is fully extended (FIG. 1A) and curved when digit 10 is flexed (FIG. 1B).

Each digit segment 12 is roughly cylindrical and fashioned from a 0.1 mm thick tube of Nitinol having a 2.64 mm outer diameter. The cylindrical walls of digit segments 12 define an axial void substantially coaxial with a digit segment axis (each digit segment axis collinear with digit axis 22) that extends from a proximal end of a digit segment 12 to a distal end of the digit segment.

Digit segment 12a and digit segment 12b each have two proximal hinge knuckles 24 and two distal hinge knuckles 26. The terminal digit segment 12c has only two proximal hinge knuckles 24. Each hinge knuckle 24 and 26 protrudes from a respective digit segment and includes a pin-accepting hole.

Digit segment 12a and digit segment 12b each have a proximal tendon guide 28 and a distal tendon guide 30. Digit segment 12c has only a proximal tendon guide 28. Tendon guides 28 and 30 are substantially the same in construction to hinge knuckles 24 and 26. The tendon-guide hole in tendon guides 28 and 30 is smaller than the pin-accepting hole of hinge knuckles 24 and 26. The tendon-guide holes in tendon guides 28 and 30 are located below and off-axis 22 and, when digit 10 is fully extended along a line perpendicular to the plane defined by hinge knuckles 24 and 26 that includes axis 22.

Hinged joint 14a is defined by a joint pin 32 passing through a pin-accepting hole through abduction adapter 20 and proximal hinge knuckles 24 of digit segment 12a.

Hinged joint 14b is defined by a joint pin 32 passing through a hole through proximal hinge knuckles 24 of digit segment 12b and distal hinge knuckles 26 of digit segment 12a.

Joint 14c is defined by a joint pin 32 passing through a hole through proximal hinge knuckles 24 of digit segment 12c and distal hinge knuckles 26 of digit segment 12b.

Tendons 16a, 16b and 16c are elongated components that are elastic in a lateral direction, that is tend to spring back to an original position when released from an applied lateral force that bends the component. Preferably, tendons 16 does not substantially lengthen when an axial stretching force is applied thereto. In some embodiments, tendons 16 are wires. In a preferred embodiment tendons 16 are of a super-elastic material such as Nitinol.

A proximal end of tendon 16a is secured to a first flexion effector (not shown) such as a flexion motor, e.g. a step motor, passes through palm 18, passes through the tendon-guide hole of proximal tendon guide 28 of digit segment 12a (below digit axis 22) and a distal end of tendon 16a is secured (e.g., by welding) to an opposite portion (above digit axis 22) of digit segment 12a so that tendon 16a passes through the plane defined by hinge knuckles 24 and 26 that includes axis 22.

A proximal end of tendon 16b is secured to a second flexion effector (not shown) such as a flexion motor, e.g., a step motor, passes through palm 18, passes through the tendon-guide hole of distal tendon guide 30 of digit segment 12a, the tendon-guide hole of proximal tendon guide 28 of digit segment 12b, the tendon-guide hole of distal tendon guide 30 of digit segment 12b, the tendon-guide hole of proximal tendon guide 28 of digit segment 12c (all below digit axis 22), and a distal end of tendon 16b is secured (e.g., by welding) to an opposite portion (above digit axis 22) of digit segment 12c so that tendon 16b passes through the plane defined by hinge knuckles 24 and 26 that includes axis 22.

Figure 1C:
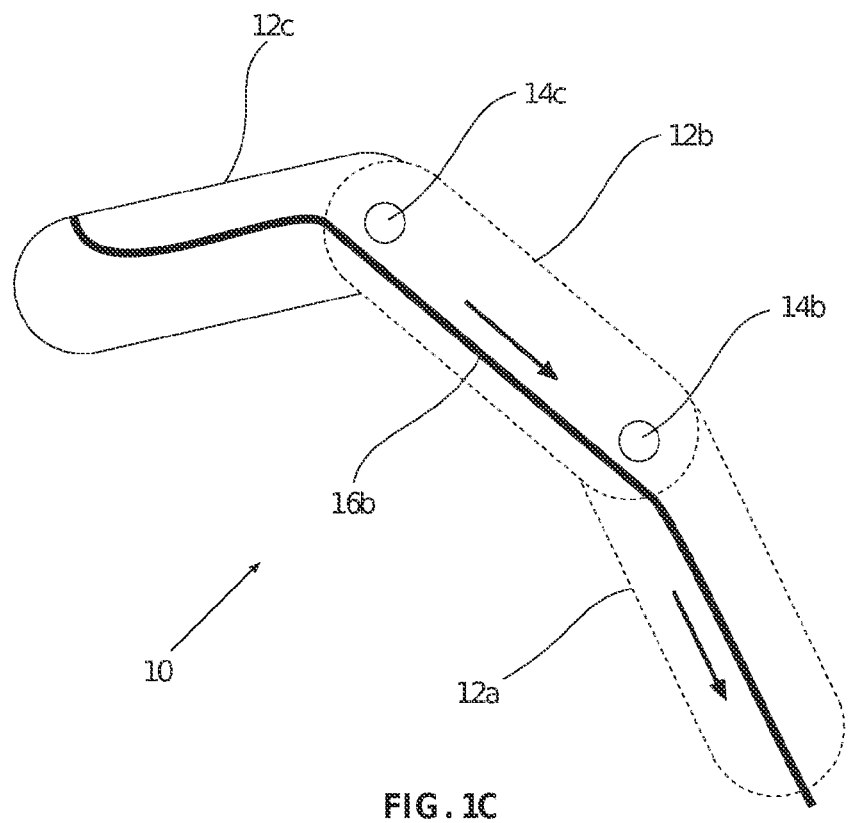
FIGS. 1C and 1D are schematic side views of the mechanical digit of FIG. 1A.
Figure 1D:
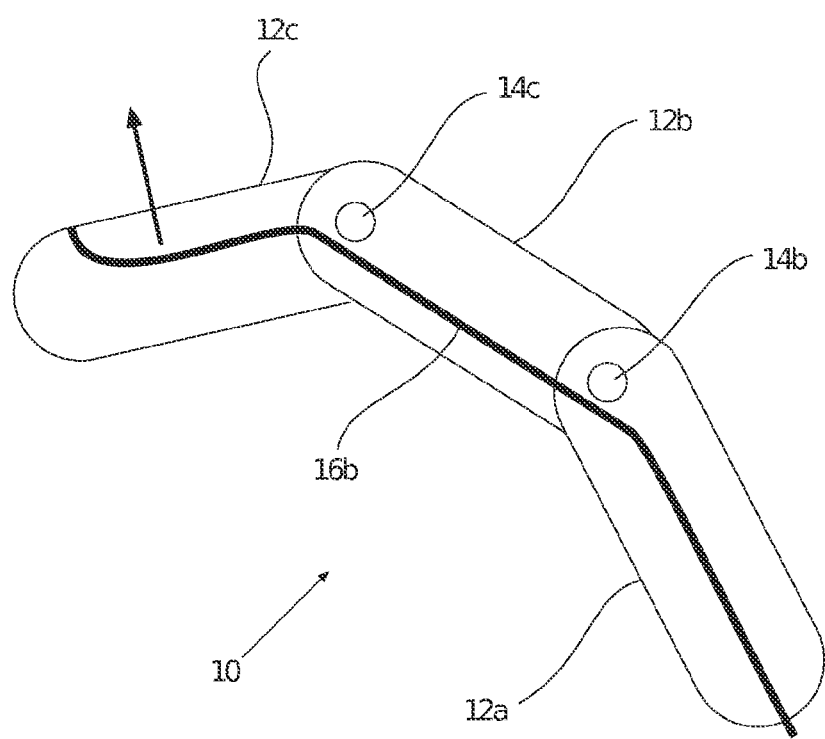

FIGS. 1C and 1D schematically illustrate flexion and extension of digit 10 around joints 14b and 14c. Referring to FIG. 1C, flexion is performed by drawing tendon 16b proximally (towards palm 18), by activation of one or more associated flexion effectors bending joints 14b and/or 14c downwards in a plane including axis 22, in the manner of a hinge. Flexion of digit 10 around joint 14a is analogously performed by drawing tendon 16a proximally. In some embodiments, tendons 16a and 16b are drawn by the same flexion effector. In some embodiments, tendons 16a and 16b are each drawn independently by a different flexion effector.

Referring to FIG. 1D, extension of digit 10 around joints 14b and 14c is performed by releasing a drawn tendon 16b, which then adopts the extended rest state depicted in FIG. 1A due to the elasticity of tendon 16b which function substantially as a spring. As a result, in some embodiments, a digit as described herein is devoid of a separate extension tendons and is operable with only flexion tendons. In some embodiments, one or more joints is provided with an extension "muscle" for example a spring or similar component that provides an additional extension force.

Generally, to provide a maximal flexion angle and greatest strength, it is preferred that tendon guides 28 and 30 maintain tendons 16a and 16b as far as possible off (below) axis 22.

Anthropomorphic Gripper

An aspect of some embodiments of the invention is an anthropomorphic gripper that is a useful as an end effector to perform tasks such as gripping and holding in a manner analogous to that of a human hand. In some embodiments, the gripper is small allowing a user to perform delicate and small tasks that would be difficult to perform manually.

According to an aspect of some embodiments of the invention there is also provided, anthropomorphic gripper, comprising: a) a palm for supporting mechanical digits, the palm having a distal end and a proximal end; and b) at least two mechanical digits as described above, secured to the palm.

In some embodiments, the palm has a palm plane and a first of the mechanical digits is attached to the palm so that the axis of the digit segments of the first digit is substantially parallel to the palm plane when the first digit is fully extended.

In some embodiments, a second of the mechanical digits is attached to the palm so that the axis of the digit segments of the second mechanical digit is substantially parallel to the palm plane when the second digit is fully extended.

In some embodiments, a second of the mechanical digits is opposable to the first of the mechanical digits, the second mechanical digit being attached to the palm so that the axis of the digit segments of the second mechanical digits substantially intersects the palm plane when the second digit is fully extended, and so that when the second digit and the first digit are flexed, it is possible to grip an object between the first digit and the second digit.

In some embodiments, the anthropomorphic gripper is configures to allow controlled abduction of at least one of the digits.

Figure 2A:
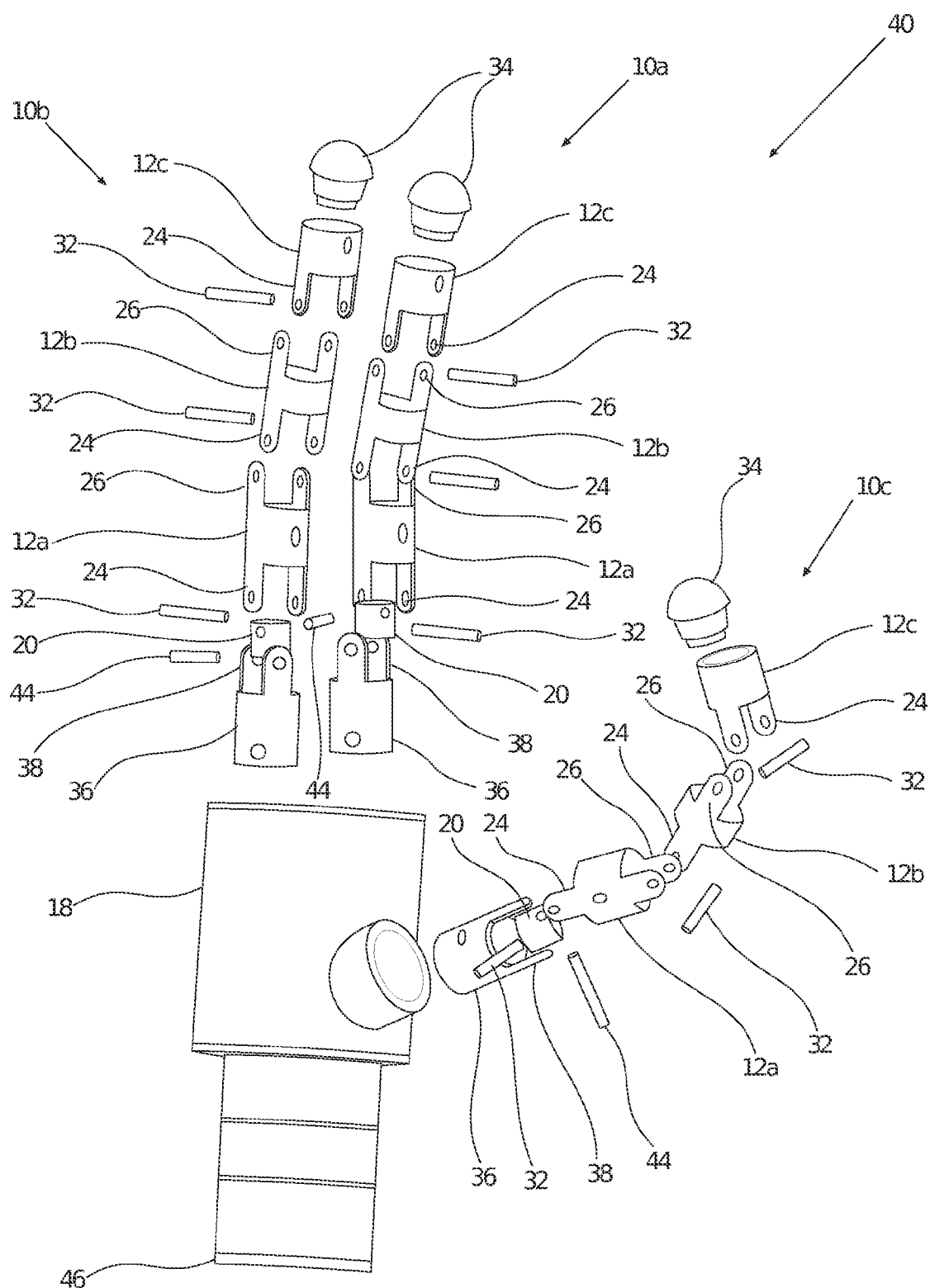
FIG. 2A is an exploded view of an embodiment of a gripper as described herein.
Figure 2B:
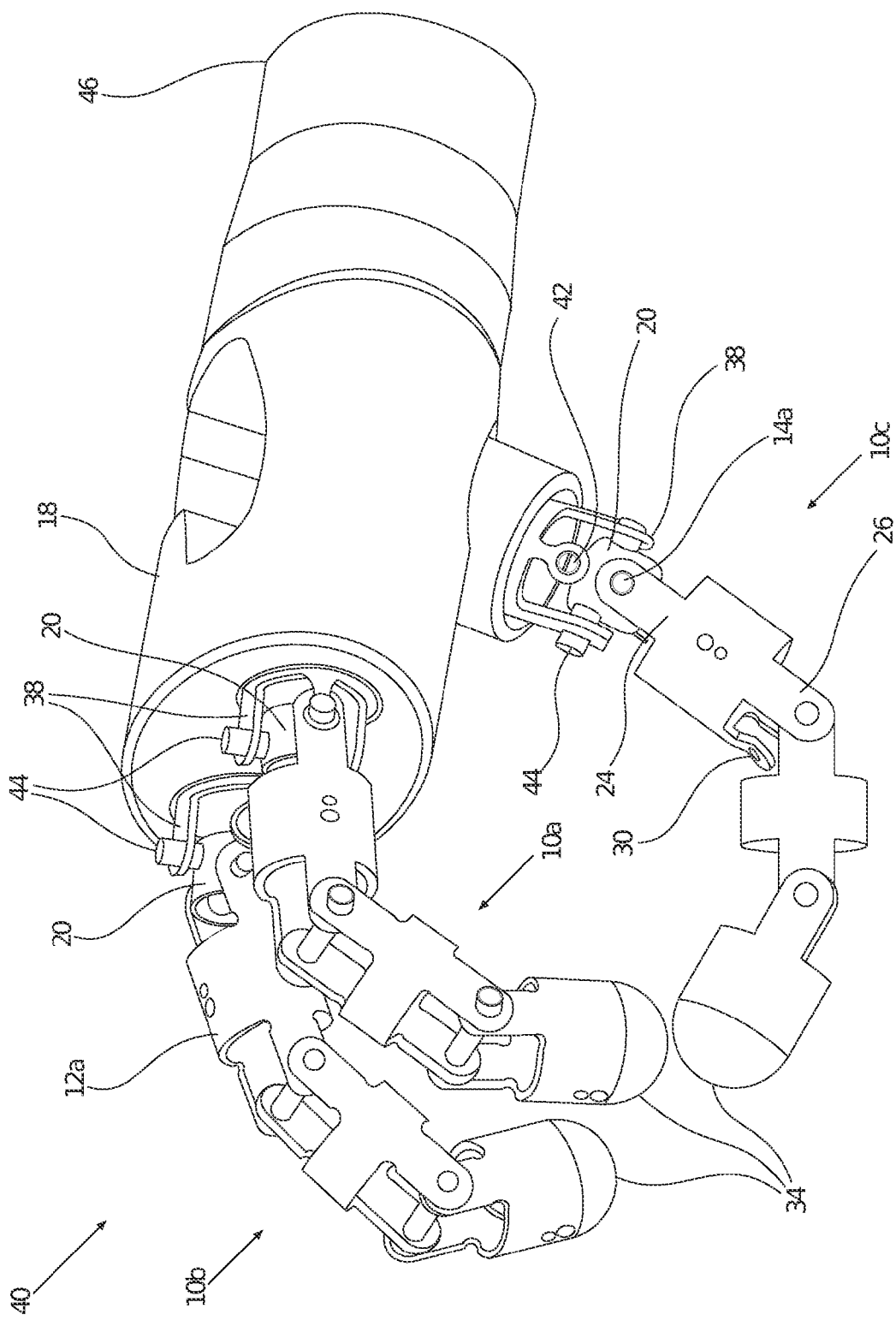
FIG. 2B is a perspective view of the gripper of FIG. 2A.

An embodiment of an anthropomorphic gripper 40 comprising three digits (finger 10a, finger 10b and thumb 10c) all three similar to digit 10 above described is depicted in FIG. 2A (exploded view) and FIG. 2B (perspective view). Fingers 10a and 10b are attached to palm 18 so that the respective digit axes 22 are substantially parallel to the plane of palm 18 when fully-extended. The axes of rotation of joints 14 of fingers 10a and 10b are oriented so that fingers 10a and 10b flex downwards from the plane of palm 18. Thumb 10c is attached to palm 18 so that the digit axis 22 substantially intersects the plane of palm 18 when thumb 10c is fully extended. The axes of rotation of joints 14 of thumb 10c are oriented so that flexion of thumb 10c is towards fingers 10a and 10b. In such a way, thumb 10c is opposable to fingers 10a and 10b, allowing an object to be gripped between thumb 10c and fingers 10a and/or finger 10b.

In addition to the digit components listed above, FIGS. 2A and 2B show digit tips 34 of silicone rubber pushed into the ends of distal digit segments 12c. FIGS. 2A and 2B also show how digits 10 attach to palm 18 through abduction adapters 20 and digit bases 36. Digit bases 36 are similar in construction to digit segments 12, and comprise a pair of distal abduction knuckles 38 and an abduction tendon guide 42. Digit bases 36 are secured in sockets in palm 18 with the help of adhesive, so that distal abduction knuckles 38 are oriented substantially 90° relative to respective hinge knuckles 24 and 26.

Each abduction adapter 20 is substantially a tube having two orthogonal pin-accepting channels near a proximal end and a distal end. Each abduction adapter 20 is rotatably secured to a digit base 36 with an abduction pin 44 that passes through a distal abduction knuckle 38 and a proximal pin-accepting channel. Each abduction adapter 20 is rotatably secured to a digit segment 12a with an abduction pin 44 that passes through a proximal hinge knuckle 24 and a distal pin-accepting channel. In such a way, a digit segment 12a, an abduction adapter 20, and a digit base 36, together constitute a cardan joint, including an abduction joint for motion in parallel to digit axis 22 (abduction of a digit relative to palm 18) and joint 14a for motion perpendicular to digit axis 22 (flexion/extension of a digit).

An abduction tendon 16c passes through palm 18, through a guide hole in abduction tendon guide 42 of digit base 36, through the void of abduction adaptor 20 to be secured (by welding) to an opposite side of the inner wall of digit segment 12a.

Figure 2C:
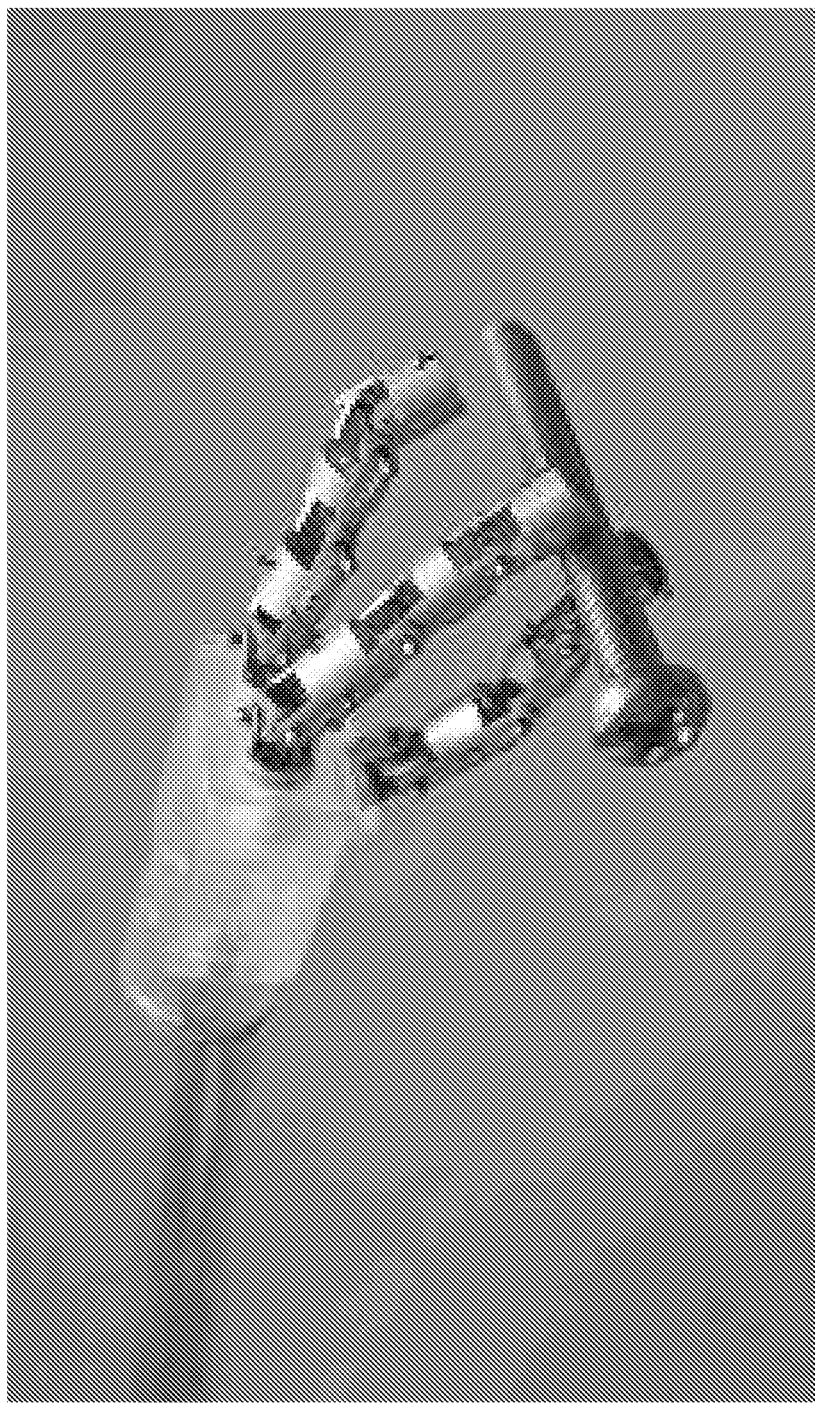
FIG. 2C is a reproduction of a photograph of an embodiment of a gripper similar to the gripper of FIG. 2A.

In a typical embodiment as seen in the photograph reproduced in FIG. 2C, some of the components of a gripper 40 as depicted in FIGS. 2A and 2B are sized and constructed as follows:

Total digit length may be approximately 16.5 mm.

Digit segments 12 may be fashioned from Nitinol tubes having an outer diameter (OD) of approximately 2.64 mm, and an inner diameter (ID) of approximately 2.22 mm. Digit 12a is approximately 6.20 mm long, has a 2.36 mm long tubular section, a 1.92 mm long distal hinge knuckle 26, and a 1.92 mm long proximal hinge knuckle 24. Digit 12b is approximately 5.20 mm long, has a 1.36 mm long tubular section, a 1.92 mm long distal hinge knuckle 26, and a 1.92 mm long proximal hinge knuckle 24. Digit 12c is approximately 3.82 mm long, has a 1.90 mm long tubular section, and a 1.92 mm long proximal hinge knuckle 24.

Digit bases 36 may be fashioned from Nitinol tubes having a OD of approximately 2.64 mm, and an ID of about 2.22 mm. The digital bases are approximately 4.82 mm long, have a 2.90 mm long tubular section, and a 1.92 mm long abduction knuckle 38.

Abduction adapter 20 may be a 1.5 mm long Nitinol tube, having a 1.6 mm OD and a 1.3 mm ID.

Joint pins 32 may be a 0.5 mm OD stainless steel tube.

Abduction pins 44 may be formed from 0.5 mm OD stainless steel tube.

Gripper palm 18 may be a 10 mm wide, 6.5 mm deep and 18 mm long carved polymer block.

Tendons 16a, 16b, 16c may be formed from 0.1 mm thick Nitinol wire.

Each of digits 10 may be flexed, by pulling a respective tendon 16a and/or 16b, and extended independently, by releasing a respective tendon 16a and/or 16b. Additionally, each of digits 10 may be adducted or abducted around the abduction joints, defined by abduction adapters 20 and abduction knuckles 38, by pulling and/or releasing an abduction tendon 16c, for example with the help of an abduction effector (e.g. a motor such as a step motor).

Each digit 10 of gripper 40 has three degrees of freedom: two flexion/extension and one abduction/adduction degree of freedom, giving gripper 40 a total of nine degrees of freedom.

In some embodiments, the fact that the flexion and abduction effectors are located remote from the digits and the grippers, and that flexion power is transmitted by tendons 16 having small dimensions, allows gripper 40 to be exceptionally small in dimension.

Method of Making a Digit

The digit segments of the digits and anthropomorphic grippers described herein are critical components that are significant in determining the physical size and cost of a digit or gripper as described herein. Any suitable method (e.g., molding, machining) may be used in making such a digit segment from any suitable material (e.g., metal, plastic, polymer).

In some embodiments, a digit segment is made by cutting from a tube of suitable material, for example, laser cutting as known in the art of stent-manufacture. Such techniques are known to be able to produce the fine detail necessary in very small dimensions. In such embodiments, a suitable tube, for example of Nitinol or Cobalt Chromium alloy is provided and cut in the appropriate size and shape, including hinge knuckles, abduction knuckles and tendon guides. In some embodiments, tendon guides cut from the tube are then bent radially inwards so that tendon guide-holes are properly oriented inside the axial void of a digit segment.

Tubes having outer diameters of 0.8 mm and even smaller that can be fashioned into three jointed digits of approximately 5 mm length are known.

Palms may be made of any suitable material (e.g., polymers, polycarbonate, metal) and using any suitable technique (e.g., molding, machining).

An advantage of some embodiments described herein is the small physical dimensions of a gripper.

In some embodiments, each digit is not more than about 10 mm wide, not more than about 7 mm wide and even not more than about 5 mm wide.

In some embodiments, each digit is not more than 50 mm long, not more than about 35 mm long and even not more than about 25 mm long.

In some embodiments, a palm digit is not more than about 22 mm wide, not more than about 16 mm wide and even not more than about 12 mm wide. For example, in the embodiment depicted in FIG. 2C, each digit is about 4 mm wide and about 20 mm long, while the palm is about 10 mm wide.

As mentioned above, using readily-available metal tubes, some embodiments include digits that are about 1 mm wide and about 5 mm long, having a palm of about 3 mm wide.

In some embodiments, a gripper is provided with a flexible glove, for example of latex rubber, silicon rubber or polyurethane elastomer. Such a glove is easily manufactured using known techniques such as dipping of a molds in a fluid precursor of an elastomer. Such a glove is useful for protecting the gripper from damage, for example from contact with abrasives (e.g., dust and grit) and fluids (water, acids, blood), for smoothing the outer surface of the gripper (especially if the glove is coated with a low-friction coating such as PTFE) and for improving grip, for example by features such as ridges or bumps on the digit tips. Such a glove is exceptionally useful in the field of surgery, especially keyhole surgery, where the glove protects parts of the body from being caught in the joints of the gripper and also protects the components from damage from parts of the body.

An anthropomorphic gripper as discussed herein may be used in any implementation, robot-controlled as well as human-controlled where such a gripper is useful, including hazardous environments (in presence of vacuum, radiation, toxic, explosive, infectious and radioactive materials) or where a small anthropomorphic gripper is useful such as surgery (especially keyhole surgery), gem-setting and assembly of MEMS. Typically, such a gripper is rotatably mounted through the palm, for example rotating around axis 22 and/or tilting axis 22.

For example, in some embodiments, a small-dimensioned gripper as described herein is an end effector component of a surgery device, especially of a surgery device useful in keyhole surgery, micro-surgery, or alternatively super-micro-surgery, such as, for example, a keyhole surgery device such as the da Vinci® surgical system (Intuitive Surgical, Inc., Sunnyvale, Calif., USA). In such embodiments, small-dimensioned grippers are introduced through small incisions (directly or through a port) and are then used to perform various gripping and tool-manipulating tasks intuitively and with relatively little training, in some embodiments providing higher precision and a lower error rate than with known end-effectors.

For example, in some embodiments, a small-dimensioned gripper as described herein is a component of a jewelry manufacture and gemstone setting device. The small dimensions of the gripper allow gripping and setting of small components such as gemstones, in some embodiments allowing greater use of less-dexterous artisans at a reduced cost and in some embodiments with fewer production losses.

For example, in some embodiments, a small-dimensioned gripper as described herein is a component of a MEMS assembly device. As known in the art, MEMS are integrated devices including mechanical components ranging up to a few millimeters in size but there are few practical devices allowing assembly of such small components.

The teachings herein have been primarily discussed with reference to anthropomorphic grippers. In some embodiments, the teachings herein may be applied for other devices, for examples stages that are substantially tables supported on two or more (generally three or more) "legs", each leg similar in construction and operating principle to the digits described herein. The use of such legs to support such a table allows the orientation of the table to be changed. Such stages are useful, for example, for supporting mirrors and other optical components, or for supporting samples such as biological samples, for example for examination using a microscope.

In some embodiments, the teachings herein are implemented in an open kinematic chain. In some embodiments, the teachings herein are implemented in a closed kinematic chain.

An anthropomorphic gripper as described herein is generally considered an end effector and is attached to an arm to constitute a tool. The arm of the tool allows the location and the orientation of the gripper to be controlled. A gripper as described herein can be attached to any arm that provides the desired range, accuracy and degrees of motion that are required for a given task. For example, in some embodiments where a gripper as described herein is used in the field of keyhole surgery, a gripper is attached to an arm of a da Vinci® surgical system (Intuitive Surgical, Inc., Sunnyvale, Calif., USA). That said, in some embodiments, especially in the field of keyhole surgery, a gripper as described herein is preferably attached to a mechanical arm as described herein.

Mechanical Arm

An aspect of some embodiments of the invention is a mechanical arm that allows movement and orientation of an attached end effector in a desired volume. An advantage of some embodiments of the mechanical arm is that movement and orientation can be effected while the attached end effector is located inside a volume accessible through a small opening. Such embodiments are exceptionally useful, for example, when a mechanical arm such is used for moving and orienting an end effector for keyhole surgery. Any suitable end effector may be attached to a mechanical arm as described herein. In some embodiments, the end effector attached to a mechanical arm as described herein is an anthropomorphic gripper as described herein.

According to an aspect of some embodiments of the invention there is also provided a mechanical arm suitable for controllably moving an end effector secured thereto, comprising:

a) an arm support base having an arm axis;
b) a hollow support rod including an axial lumen parallel to the arm axis, fixedly secured to and extending distally from the arm support base;
c) a hollow extension unit including an axial lumen, secured to a distal end of the hollow support rod with a joint constituting a hinged elbow joint, where when the elbow joint is straight, the axial lumen of the hollow extension unit is substantially collinear with the axial lumen of the hollow support rod;
d) an upper rotating rod rotatably contained within the axial lumen of the hollow support rod having a distal end secured to a proximal end of a double cardan joint drive shaft substantially contained inside the elbow joint;
e) a lower rotating rod rotatably contained within the axial lumen of the hollow extension unit, a proximal end of the lower rotating rod secured to a distal end of the double cardan joint drive shaft, thereby rotatingly linking the lower rotating rod with the upper rotating rod through the double cardan joint drive shaft; and
f) a wrist shell fixedly secured to a distal end of the lower rotating rod wherein axial rotation of a proximal end of the upper rotating rod leads to axial rotation of the lower rotating rod and the wrist shell substantially irrespective of an angle of the elbow joint.

In some embodiments, the mechanical arm further comprises a mechanism to effect controlled bending of the elbow joint.

In some embodiments, a proximal end of the upper rotating rod extends proximally from a proximal end of the hollow support rod.

In some embodiments, the mechanical arm further comprises a rotation motor secured to the arm support base and functionally associated with the proximal end of the upper rotating rod, allowing rotation of upper rotating rod, double cardan joint drive shaft and lower rotating rod when the motor is activated.

In some embodiments, the rotation motor is slidingly secured to the support base, allowing the rotation motor to slide in parallel to the arm axis relative to the support base.

In some embodiments, the upper rotating rod is slidingly associated with the rotation motor, allowing the upper rotating rod to move in parallel to the arm axis relative to the rotation motor.

FIGS. 3A, 3B, 4A and 4B depicts an embodiment of a mechanical arm 50 as described herein including an elbow joint 52 configured to move in one plane around an elbow axis 54. Arm 50 also includes a wrist joint 56 configured to move in one plane around a wrist axis to which is attached an end effector, an embodiment of an anthropomorphic gripper 40 substantially as described above. Arm 50 is also configured to allow axial rotation of an attached end effector.

Arm 50 allows a user to move an end-effector such as gripper 40 in a desired volume with a desired orientation, for example to manipulate or grip some object. Some embodiments of an arm as described herein such as arm 50 provide three types or ranges of motion: bend around an elbow axis 54 at an elbow joint such as 52, bend around a wrist axis 58 at a wrist joint such as 54, and axial rotation of the end-effector. Importantly, such motion can be effected while the attached end effector is located inside a volume accessible through a small opening.

On a base 60 of arm 50 is supported a slider motor 62 which is connected to and controls the motion and position of a projecting rod 64, such that activation of slider motor 62 causes projecting rod 64 to move in parallel to arm axis 66, as shown by the arrow on slide motor 62.

Supported on base 60 of arm 50 is also a rotation motor 68 which is connected to and controls the motion and position of an upper rotating rod 70, which rotates around arm axis 66 upon activation of rotation motor 68.

A hollow support rod 72 including a lumen parallel to arm axis 66 is attached to the bottom of base 60 and extends distally as far as elbow joint 52 in parallel to arm axis 66.

As noted above, elbow joint 52 is a hinge configured to move in one plane around elbow axis 54 that connects between the distal end of hollow support rod 72 and a proximal end of a hollow extension unit 74 that includes an axial lumen.

A sliding sleeve member 76 slidingly fits around hollow support rod 72. A proximal end of sliding sleeve member 76 is mechanically linked to projecting rod 64 through linker 78.

A proximal end of a rigid connecting rod 80 is attached with a hinge to a distal end of sliding sleeve member 76 and a distal end of rigid connecting rod is attached with a hinge to a proximal end of hollow extension unit 74.

Palm 18 of gripper 40 is attached to wrist shell 82 through wrist joint 56.

Upper rotating rod 70 is rotatably contained inside the axial lumen of hollow support rod 72 while a lower rotating rod 84 is rotatably contained inside the axial lumen of hollow extension unit 74. Connecting the distal end of upper rotating rod 70 and the proximal end of lower rotating rod 84 is a double cardan joint drive shaft 86 located inside elbow joint 52 including a proximal cardan joint 88 and a distal cardan joint 90 and a intermediate cardan shaft 92. In the Figured, distal cardan joint 90 is not seen.

The distal end of lower rotating rod 84 passes through and extends beyond the distal end of the axial lumen of hollow extension unit 74 to be fixedly attached to wrist shell 82.

Figure 4A:
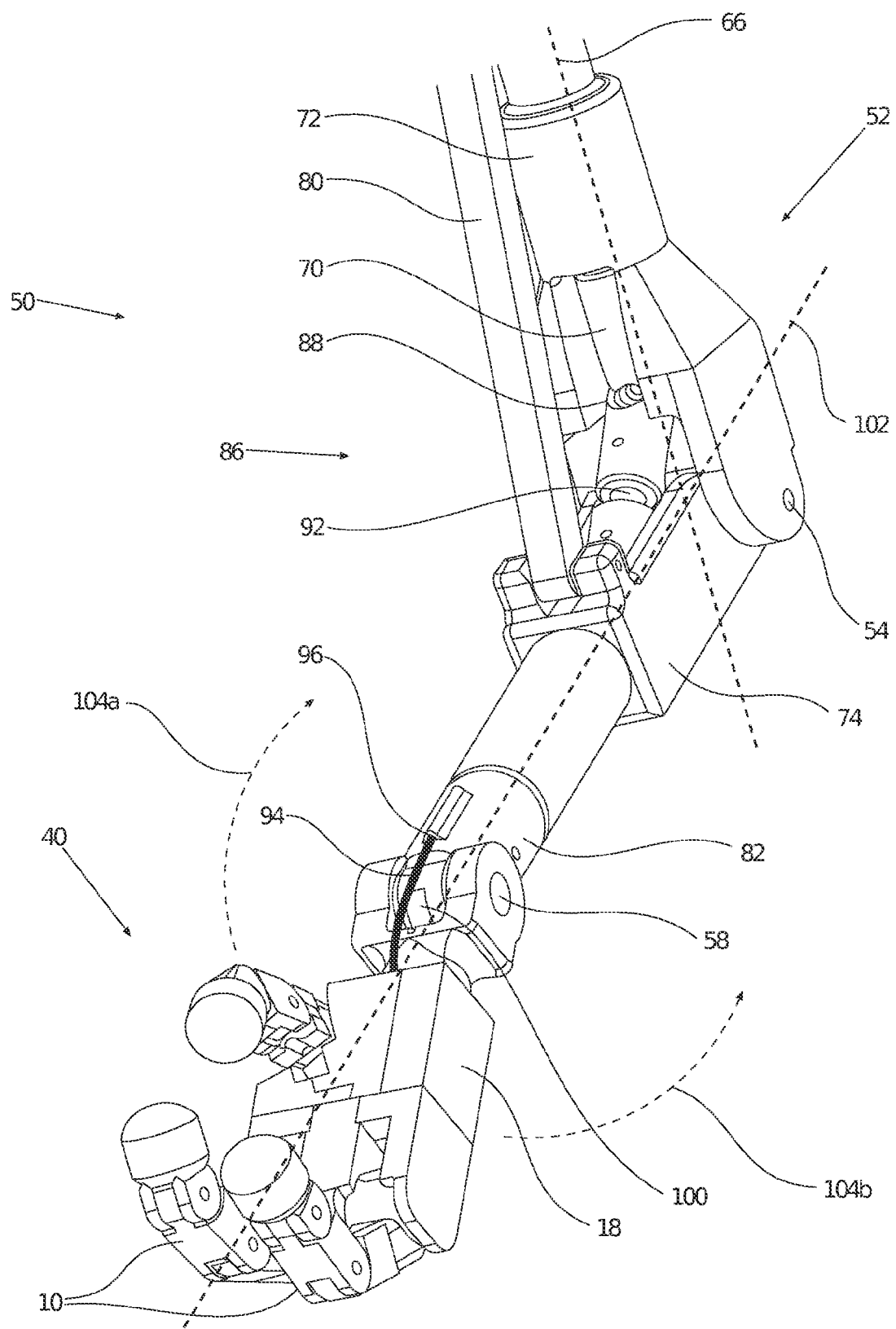
FIG. 4A is a perspective view of the mechanical arm of FIG. 3A, showing a closer view of the gripper and the elbow.
Figure 4B:
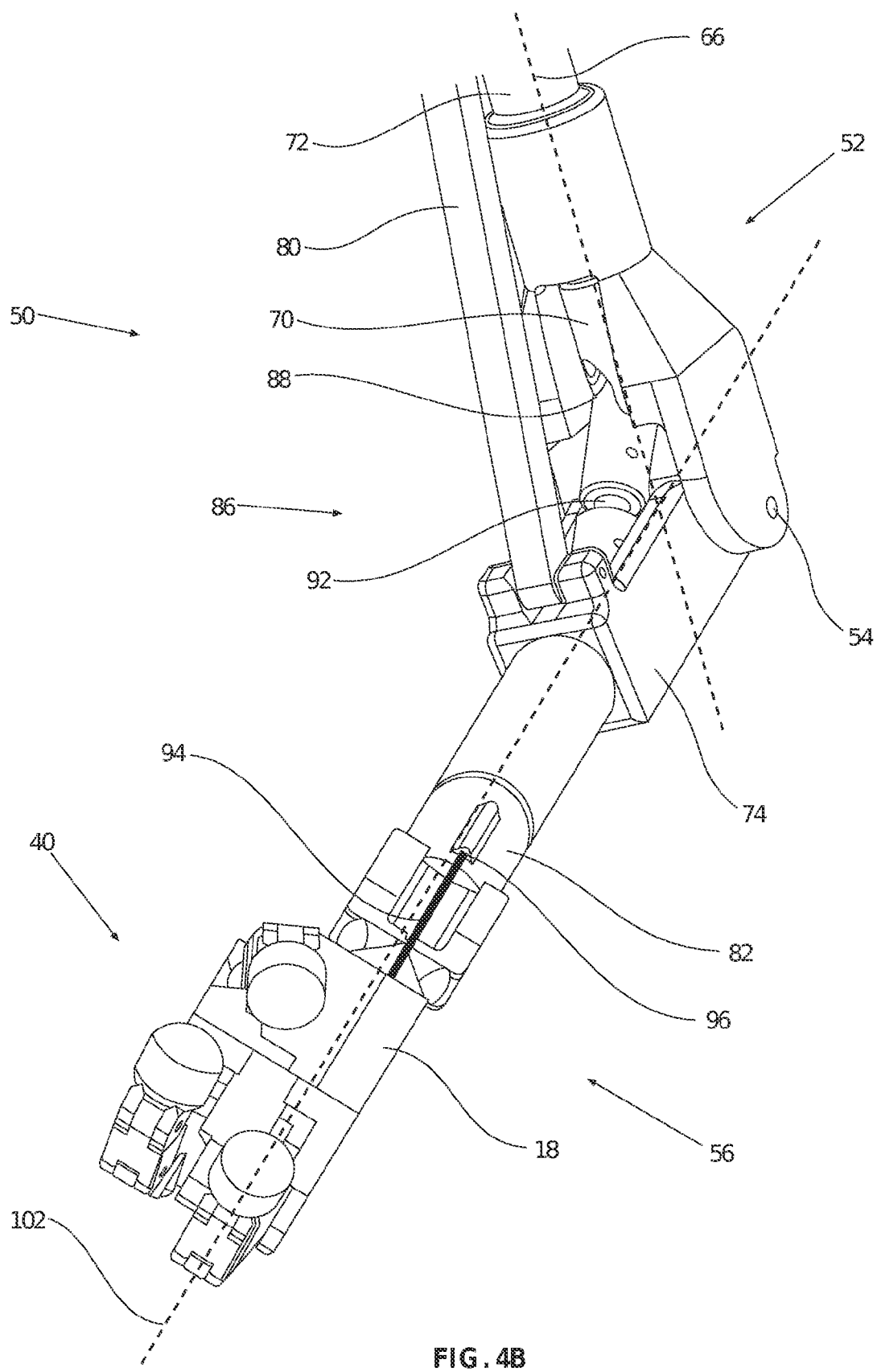
FIG. 4B is another view of the mechanical arm of FIG. 4A, in which the wrist is turned.

As seen in FIGS. 4A and 4B, a distal end of an inner wrist tendon 94, substantially a wire similar to tendons 16 as described above, is secured to the proximal end (base) of palm 18. Inner wrist tendon 94 crosses wrist joint 56, enters a hole 96 in the side of wrist shell 82 and passes through axial lumina of lower rotating rod 84, intermediate cardan shaft 92 and upper rotating rod 70. The distal end of inner wrist tendon 94 exits the axial lumen of upper rotating rod 70 at proximal end 98 of upper rotating rod 70.

Not depicted is an outer wrist tendon that is located on the side of wrist joint 56 opposite inner wrist tendon 94, crosses wrist joint 54, enters a hole in the opposite side of wrist shell 82 to pass through axial lumina of lower rotating rod 84, intermediate cardan shaft 92 and upper rotating rod 70 so that the distal end of the outer wrist tendon exits the axial lumen of upper rotating rod 70 at proximal end 98 of upper rotating rod 70.

Not seen in FIGS. 4A and 4B are tendons 16 of each one of digits 10 (a total of nine tendons) that pass through proximal end 46 of palm 18, through an axial hole 100 in wrist shell 82 to enter the axial lumen of lower rotating rod 84 and then, similarly to inner wrist tendon 94 and the outer wrist tendon, pass through the axial lumina of lower rotating rod 84, intermediate cardan shaft 92 and upper rotating rod 70. The distal ends of the nine digit tendons 16 exits the axial lumen of upper rotating rod 70 at proximal end 98 of upper rotating rod 70.

The distal ends of the eleven tendons are each functionally associated with a respective effector (not depicted) such as a motor, especially a step motor.

Figure 3A:
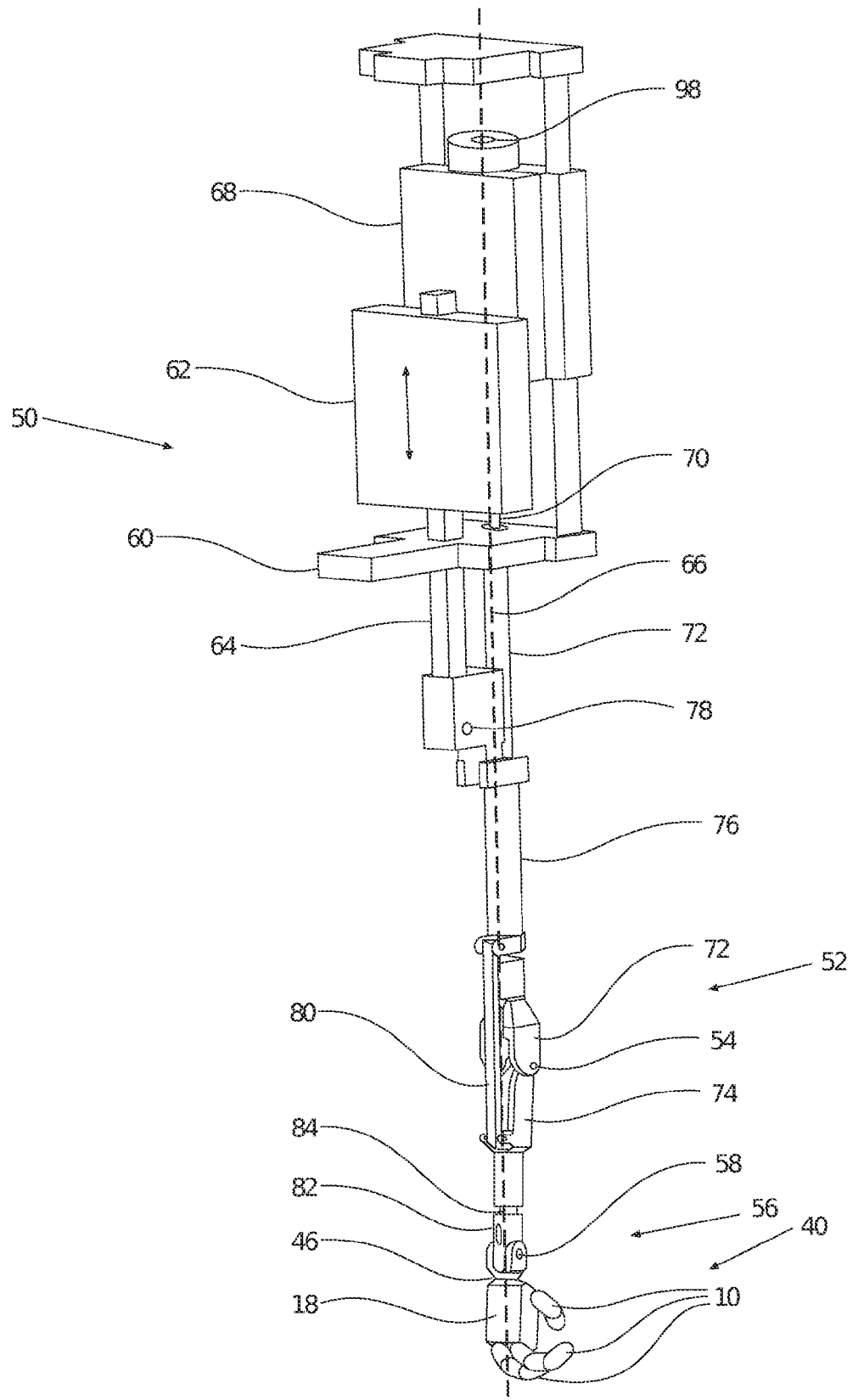
FIG. 3A is a perspective view of an embodiment of a mechanical arm as described herein, bearing an embodiment of a mechanical gripper as described herein.
Figure 3B:
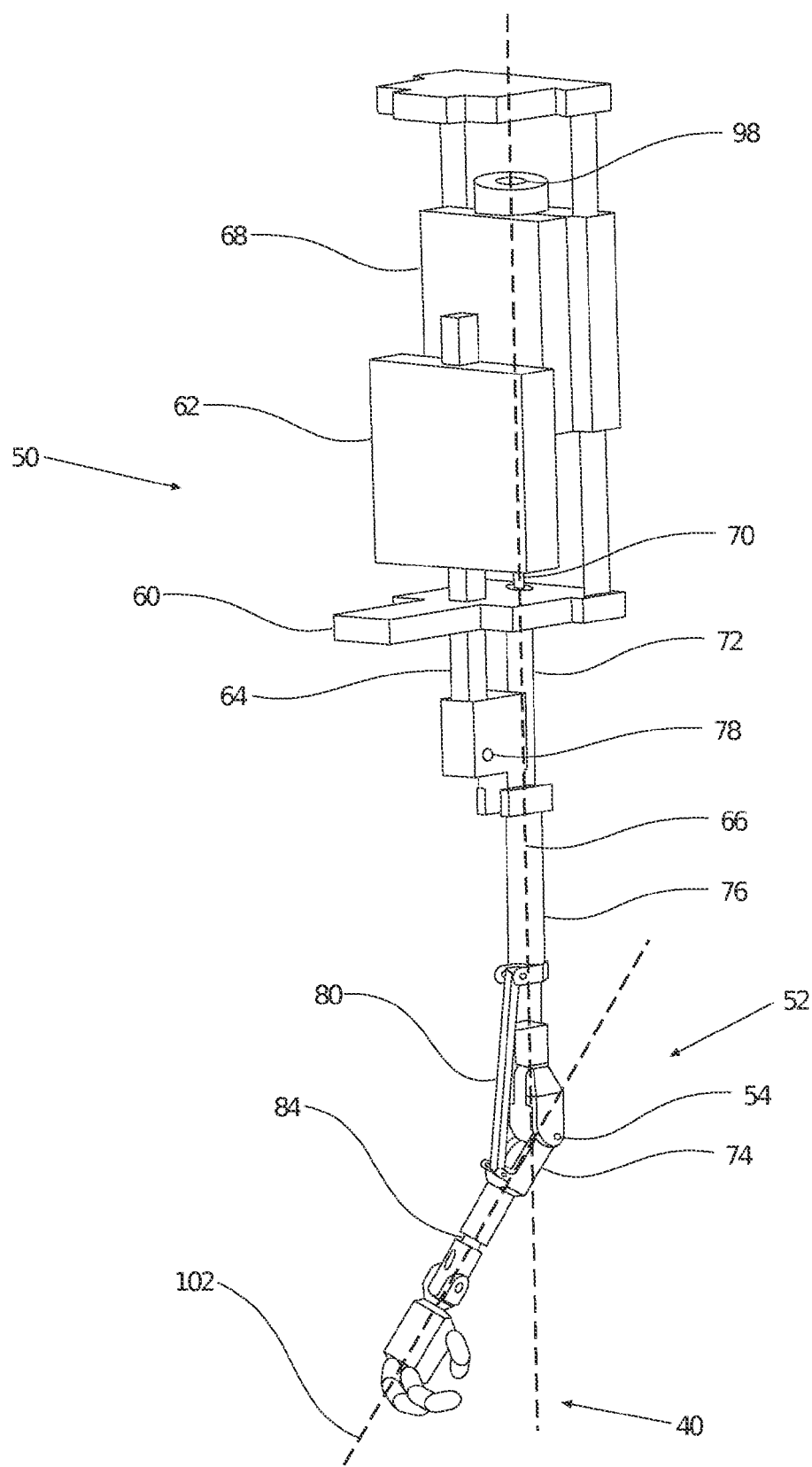
FIG. 3B is a perspective view of the mechanical arm of FIG. 3A, in which the elbow is bent.

Taken together, FIGS. 3A and 3B illustrate bending of arm 50 at elbow joint 52.

In FIG. 3A, slider motor 62 is in a state where projecting rod 64 is at an extreme distal position so that sliding sleeve member 76 is also at an extreme distal position and consequently hollow support rod 72 and hollow extension unit 74 are collinear and parallel with arm axis 66. Arm 50 is in a fully extended configuration.

When slider motor 62 is activated to draw projecting rod 64 axially in a proximal direction, projecting rod 64 pulls sliding sleeve member 76 in a proximal direction through the mechanical linkage. The proximal end of connecting rod 80 is pulled in a proximal direction, lifting the distal end of connecting rod 80, which leads to bending of elbow joint 52 of arm 50 around elbow axis 54.

Analogously, when slider motor 62 is activated to push projecting rod 64 axially in a distal direction, elbow joint 52 of arm 50 straightens around elbow axis 54.

FIGS. 4A and 4B together illustrate axial rotation of gripper 40. Rotation motor 68 is activated (clockwise or counterclockwise) to rotate upper rotating rod 70 inside the axial lumen of hollow support rod 72, leading to rotation of lower rotating rod 84 inside hollow extension unit 74 through double cardan joint drive shaft 86 inside elbow joint 52. As wrist shell 82 is secured to the distal end of lower rotating rod 84, gripper 40 rotates around an axis 102 collinear with lower rotating rod 84.

Flexing of wrist joint 56 around wrist axis 58 is performed by activating the respective effectors of inner wrist tendon 94 and of the outer wrist tendon in opposite directions. For example, to flex wrist joint 56 upwards (104a in FIG. 4A), inner wrist tendon 94 is pulled in a proximal direction while the outer wrist tendon is released to allow distal movement. For example, to flex wrist joint 56 downwards (104b in FIG. 4A), the outer wrist tendon is pulled in a proximal direction while inner wrist tendon 94 is released to allow distal movement. In some embodiments, inner wrist tendon 94 and the outer wrist tendon each have a different effector. In some embodiments, inner wrist tendon 94 and the outer wrist tendon share a same effector, and includes a "see-saw" connector to simultaneously pull one wrist tendon in a proximal direction while distally releasing the other tendon.

The motion of digits 10 is substantially as described above and substantially includes activation of a respective effector to proximally pull an associated tendon 16 (e.g., to flex a digit) or by activation of a respective effector to distally release a pulled tendon (e.g., to allow extension of a flexed digit).

It is important to note that, in some embodiments, each motion is substantially independent and substantially unaffected by the other motions. For example, axial rotation of an end effector by activation of rotation motor 68 can be performed at substantially any angle of elbow joint 52 due to double cardan joint drive shaft 86. In this context it is important to note that in some embodiments, bending of elbow joint 52 may lead to some translation of double cardan joint drive shaft 86 that may lead to locking of double cardan joint drive shaft 86. In some embodiments, an arm such as 50 includes a feature to avoid such drive shaft locking. For example, in some embodiments, rotation motor 68 is slidingly secured to base 60, allowing linear motion of rotation motor 68 relative to elbow joint 52 in parallel to arm axis 66. Alternatively, in some embodiments, upper rotating rod 70 is slidingly associated with rotation motor 68, allowing linear motion of upper rotating rod 70 relative to rotation motor 68 in parallel to arm axis 66.

As noted above, in some embodiments such movement and orientation can be effected while an attached end effector is located inside a volume accessible through a small opening, a feature useful, for example, in keyhole surgery. Specifically, in some embodiments, a sliding sleeve member 76 is positioned in the small opening so that bulky components such as base 60 and motors 62 and 68 are located outside of the volume, while the relatively small portions of the arm and the end effector are located inside the volume. While inside the small opening sliding sleeve member 76 may be moved axially to bend elbow joint 52 as described above, substantially without limitation, allowing substantially unlimited operation of the arm and of the end effector.

Orientation Controller

An aspect of the invention is a mechanical orientation controller based on a parallelogram linkage useful, for example, for controlling the orientation of an end effector attached to the orientation controller. In some embodiments, the orientation controller allows independent rotational motion around two axes (pitch and roll).

Any suitable end-effector or tool may be attached to a mechanical orientation controller as described herein. In some embodiments, an end-effector attached to an orientation controller is an anthropomorphic gripper as described herein. In some embodiments, a tool attached to an orientation controller as described herein is a mechanical arm as described herein to which an end effector such as an anthropomorphic gripper as described herein is attached.

According to an aspect of some embodiments of the invention there is also provided an orientation controller, comprising:

a) a base;

b) an orientation control linker defining a fixed longitudinal distance between a pivot point and an orientation transmission point, including a longitudinal axis between the pivot point and the orientation transmission point, the pivot point attached to the base through a joint allowing rotary motion relative to the base around the longitudinal axis and around a transverse axis perpendicular to the longitudinal axis;

c) extending from a proximity to the orientation transmission point in a substantially vertical direction, at least three rigid orientation transmission rods of substantially equal length, a proximal end of each orientation transmission rod linked to the orientation control linker through a joint allowing rotary motion relative to the orientation transmission point, wherein the proximal ends define a closed curve surrounding the orientation transmission point; and d) an orientation reception linker including an orientation reception point and a longitudinal axis parallel to the longitudinal axis of the orientation control linker, linked to a distal end of each orientation transmission rod through a joint allowing rotary motion relative to the orientation reception point, so that the orientation transmission rods are parallel.

In some embodiments, the components of the orientation controller constitute two orthogonal parallelogram linkages: a first parallelogram linkage functional for transferring transverse rotation of the orientation control linker to transverse rotation of the orientation reception linker comprising as vertices the pivot point, the orientation transmission point, the orientation reception point and a stationary point located at the intersection of the longitudinal axis of the orientation reception linker and a vertical axis passing through the pivot point and parallel to the orientation transmission rods; and a second parallelogram linkage functional for transferring longitudinal rotation of the orientation control linker to the orientation reception linker comprising as vertices the distal ends and the proximal ends of the orientation transmission rods located at a transverse dimension of the closed curve.

In some embodiments, the orientation control linker is substantially straight between the pivot point and the orientation transmission point. That said, the orientation control linker may be of any suitable shape, for example curved or bowed.

In some embodiments, the orientation controller comprises at least one effector (e.g., a motor such as step motor) to rotate the orientation control linker around the transverse axis around the pivot point.

In some embodiments, the orientation controller comprises at least one effector (e.g., a motor such as step motor) to rotate the orientation control linker around the longitudinal axis around the pivot point.

In some embodiments, the orientation transmission point is in the center of the closed curved defined by the proximal ends of the orientation transmission rods. In some embodiments, the proximal ends of the orientation transmission rods are equidistant from the orientation transmission point. In some embodiments, the orientation controller comprises only three orientation transmission rods and the closed curve is a triangle, for example an equilateral or isosceles triangle. In some embodiments, the orientation controller comprises only four orientation transmission rods, and the closed curve is, for example, a rectangle, a square, a parallelogram, a kite or a rhombus.

In some embodiments, the dimension of the closed curve is not more than about 30%, not more than about 20%, not more than about 10%, not more than about 5% and even not more than about 3%, the distance between the pivot point and the orientation transmission point. By "dimension of the closed curve" is meant the diameter of the smallest circle that can completely encircle the closed curve. In some embodiments, the small dimensions are advantageous in allowing the orientation controller to be more compact and less cluttering.

In some embodiments, the orientation controller further comprises a rigid support rod of a length substantially equal to that of the orientation transmission rods, which proximal end is attached to the orientation control linker at the orientation transmission point through a joint allowing rotary motion and which distal end is attached to the orientation reception linker at the orientation reception point through a joint allowing rotary motion.

In some embodiments, the orientation controller further comprises a tool secured to the orientation reception linker so that a portion of the tool is coincident with the stationary point.

In some embodiments, the orientation controller further comprises an elongated rigid connecting arm extending from the orientation reception linker. In some embodiments, a portion of the connecting arm extends at an angle diverging from the longitudinal axis of the orientation reception linker. In some embodiments, a portion of the connecting arm extends at an angle diverging from the longitudinal axis of the orientation reception linker. In some embodiments, a portion of the connecting arm is substantially distant from the longitudinal axis of the orientation reception linker. In some embodiments, the connecting arm is substantially coplanar with the longitudinal axis of the orientation reception linker.

An embodiment of an orientation controller, orientation controller 106 is described with reference to FIGS. 5 through 8.

Figure 5A:
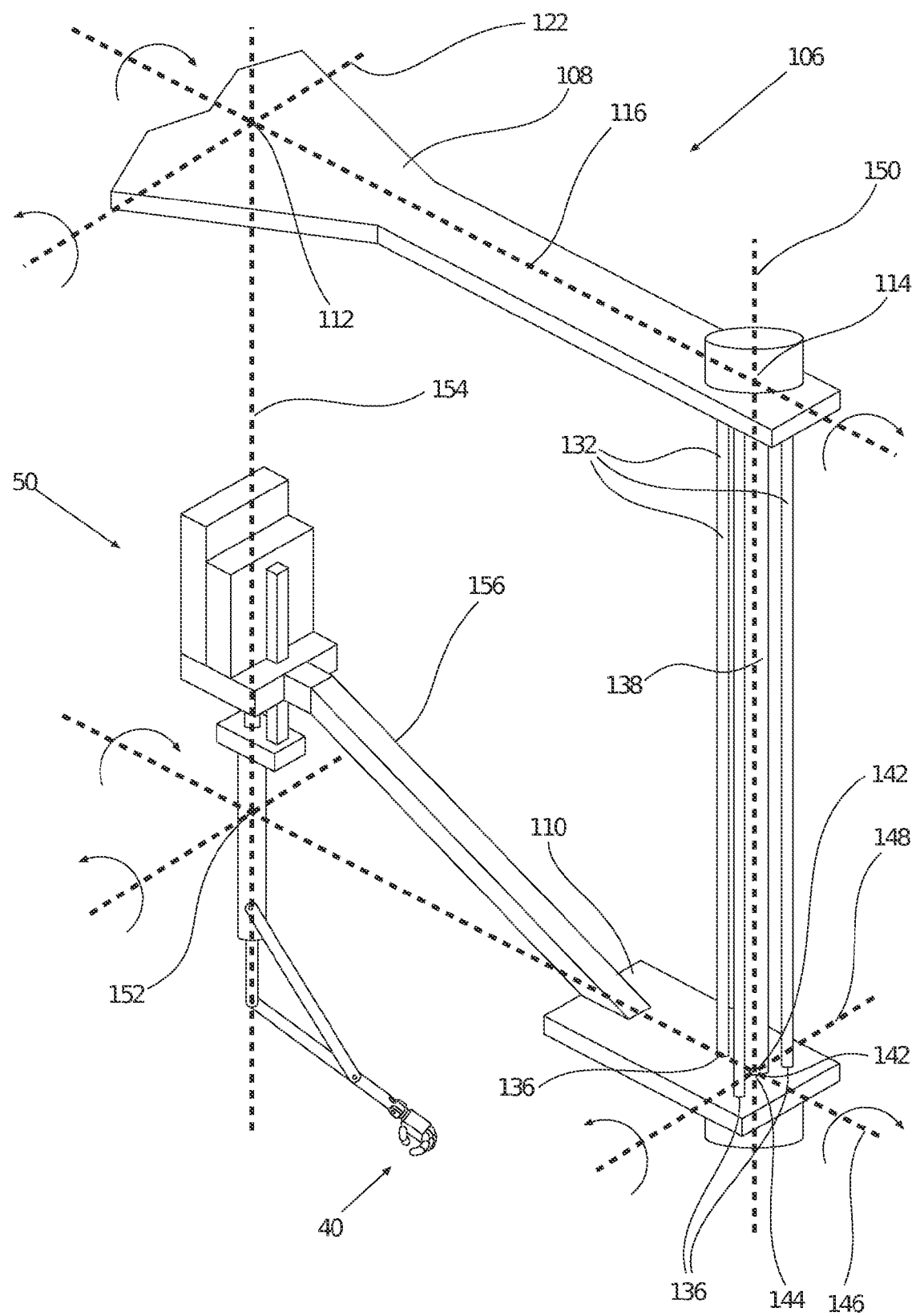
FIG. 5A is a perspective view of an embodiment of a orientation controller as described herein to which a mechanical arm bearing a mechanical gripper of FIG. 3A.

In FIG. 5A orientation controller 106 is depicted with an attached mechanical arm 50 as described above with an anthropomorphic gripper 40 as described above. For clarity, some details and components of orientation controller 106 are omitted from the figure. Orientation controller 106 includes an orientation control linker 108 and a orientation reception linker 110.

In device 106, orientation control linker 108 is a rigid planar Y-shaped sheet (e.g., of stainless steel) defining a fixed longitudinal distance between a pivot point 112 and an orientation transmission point 114, including a longitudinal axis 116 between pivot point 112 and orientation transmission point 114. Pivot point 112 of orientation control linker 108 is attached to an orientation controller base 118 through a ball joint 120 allowing longitudinal axis rotation (roll around longitudinal axis 116) and transverse axis rotation (pitch around a transverse axis 122 perpendicular to longitudinal axis 116) relative to base 118.

Secured to orientation controller base 118 are two tilt motors 124a and 124b (e.g., step motors) each configured to controllably rotate an associated tilt wheel 126a or 126b, respectively, through about 90° (0°±45°). Tilting arm 128a is attached to both the periphery of tilt wheel 126a and an edge of orientation control linker 108 through ball joints 130. Similarly, tilting arm 128b is attached to both the periphery of tilt wheel 126b and an edge of orientation control linker 108 through ball joints 130. As is discussed in detailed hereinbelow, tilt motors 124, tilt wheels 126 and tilting arms 128 together constitute effectors that allow controlled longitudinal and transverse axis rotation of orientation control linker 108.

Extending from a proximity to orientation transmission point 114 in a substantially vertical direction, are three rigid orientation transmission rods 132 of substantially equal length, a proximal end 134 of each transmission rod attached to orientation control linker 108 through a joint allowing rotary motion (e.g., a ball joint), wherein the three proximal ends 134 of orientation transmission rods 132 define a closed curve surrounding orientation transmission point 114, in orientation controller 106, an isosceles triangle, where orientation transmission point 114 is in the center of the closed curve and equidistant from each one of proximal ends 134. The dimension of the isosceles triangle (the diameter of a circle encircling the triangle) is 10% of distance between pivot point 112 and orientation transmission point 114.

Positioned between the three orientation transmission rods is rigid support rod 138 having substantially the same length as orientation transmission rods 132. A proximal end 140 of support rod is attached to orientation control linker 108 at orientation transmission point 114 through a joint allowing rotary motion (e.g., a ball joint).

In device 106, orientation reception linker 110 is a rigid planar rectangular block (e.g., of stainless steel) with a width similar to that of orientation control linker 108 in proximity to orientation transmission point 114 but which length is substantially shorter than the length of orientation control linker 108. Orientation reception linker 110 is attached to orientation transmission rods 132 and support rod 138 through a joint allowing rotary motion (e.g., a ball joint) so that all four rods are parallel. Consequently, a distal end 142 of support rod 138 is attached at an orientation reception point 144 of orientation reception linker 110 while distal ends 136 of orientation transmission rods 132 are arrayed around reception point 144 in the same way as proximal ends 134 are arrayed around orientation transmission point 114, and isosceles triangle. Orientation reception linker 110 has a longitudinal axis 146 parallel to longitudinal axis 116 of orientation control linker 108 and a transverse axis 148 parallel to transverse axis 122 of orientation control linker 108.

An orientation transmission vertical axis 150 is defined between orientation transmission point 114 and orientation reception point 144, collinear with support rod 138.

The above-described assembly substantially constitutes two orthogonal parallelogram linkages.

The first parallelogram linkage is functional for transferring transverse rotation (pitch, rotation around transverse axis 122) of orientation control linker 108 to transverse rotation of orientation reception linker 110 (rotation around transverse axis 148). The vertices of the first parallelogram linkage are pivot point 112, orientation transmission point 114, orientation reception point 144 and a virtual stationary point 152 located at the intersection of longitudinal axis 146 and a vertical axis 154 passing through pivot point 112 in parallel to orientation transmission rods 132.

The second parallelogram is functional for transferring longitudinal rotation (roll, rotation around longitudinal axis 116) of orientation control linker 108 to longitudinal rotation (roll, rotation around longitudinal axis 146) of orientation reception linker 110. The vertices of the second parallelogram linkage are the distal ends 136 and proximal ends 134 of orientation transmission rods 132 located at the transverse dimension of the closed curve described above. Specifically, two vertices are located at proximal ends 134 of the two orientation transmission rods 132 that are furthest away from vertical axis 150 in the transverse direction while two vertices are located at distal ends 136 of the two orientation transmission rods 132 that are furthest away from vertical axis 150 in the transverse direction.

A proximal end of rigid elongated connecting arm 156 is rigidly connected to orientation reception linker 110 and extends upwards and away from orientation reception linker 110, being coplanar with but diverging from longitudinal axis 146.

A mechanical arm 50 bearing an anthropomorphic gripper 40 is connected to a distal end of connecting arm 156 in such a way that stationary point 152 is located inside sliding sleeve member 76.

Although not depicted in the figures, orientation controller base 118 is immovably secures to a supporting structure, for example to a girder or a wall. Although not depicted, tendons (16, 94) required for operating arm 50 and gripper 40 as well as control lines for operating motors 62 and 68 pass from arm 50, along connecting arm 156, along orientation transmission rods 132, along orientation control linker 108 to respective effectors and actuators located in proximity of orientation controller base 118.

Orientation controller 106 can be used to control the angular orientation of mechanical arm 50 and anthropomorphic gripper 40 around stationary point 152 by transferring motion from orientation control linker 108, through orientation transmission rods 132, orientation reception linker 110 and connecting arm 156.

Figure 5B:
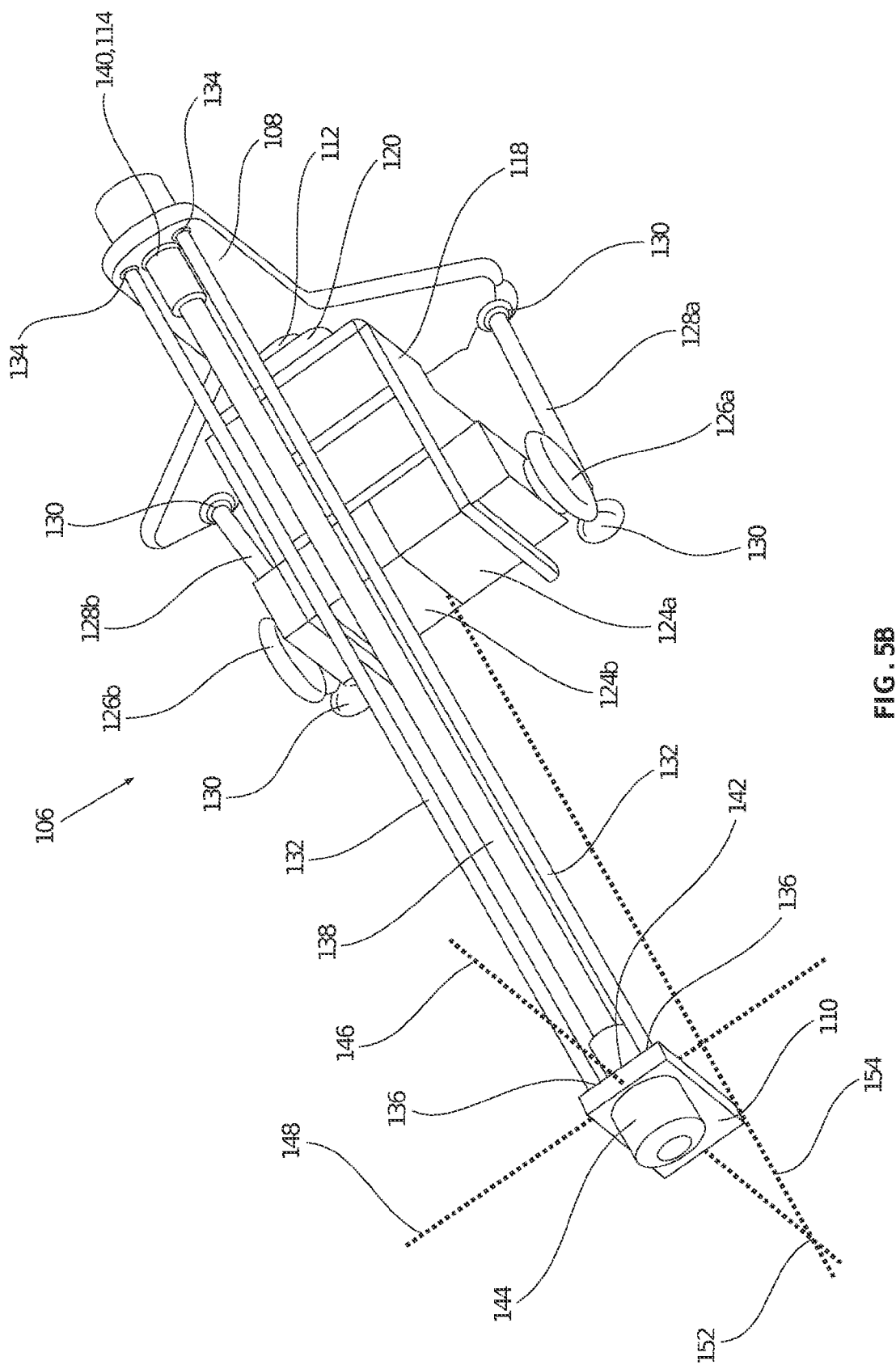
FIG. 5B is a perspective view of the orientation controller of FIG. 5A.

For example, in a rest position as depicted in FIGS. 5A and 5B, both tilt motors 124 are set so that respective tilt wheels 126 are oriented at 0°, orientation control linker 108 is level so that longitudinal axis 116 and transverse axis 122 are perpendicular to vertical axis 154 and orientation reception linker 110 is level so that longitudinal axis 146 and transverse axis 148 are perpendicular to orientation transmission vertical axis 150. Arm axis 66 is collinear with vertical axis 154.

Figure 6A:
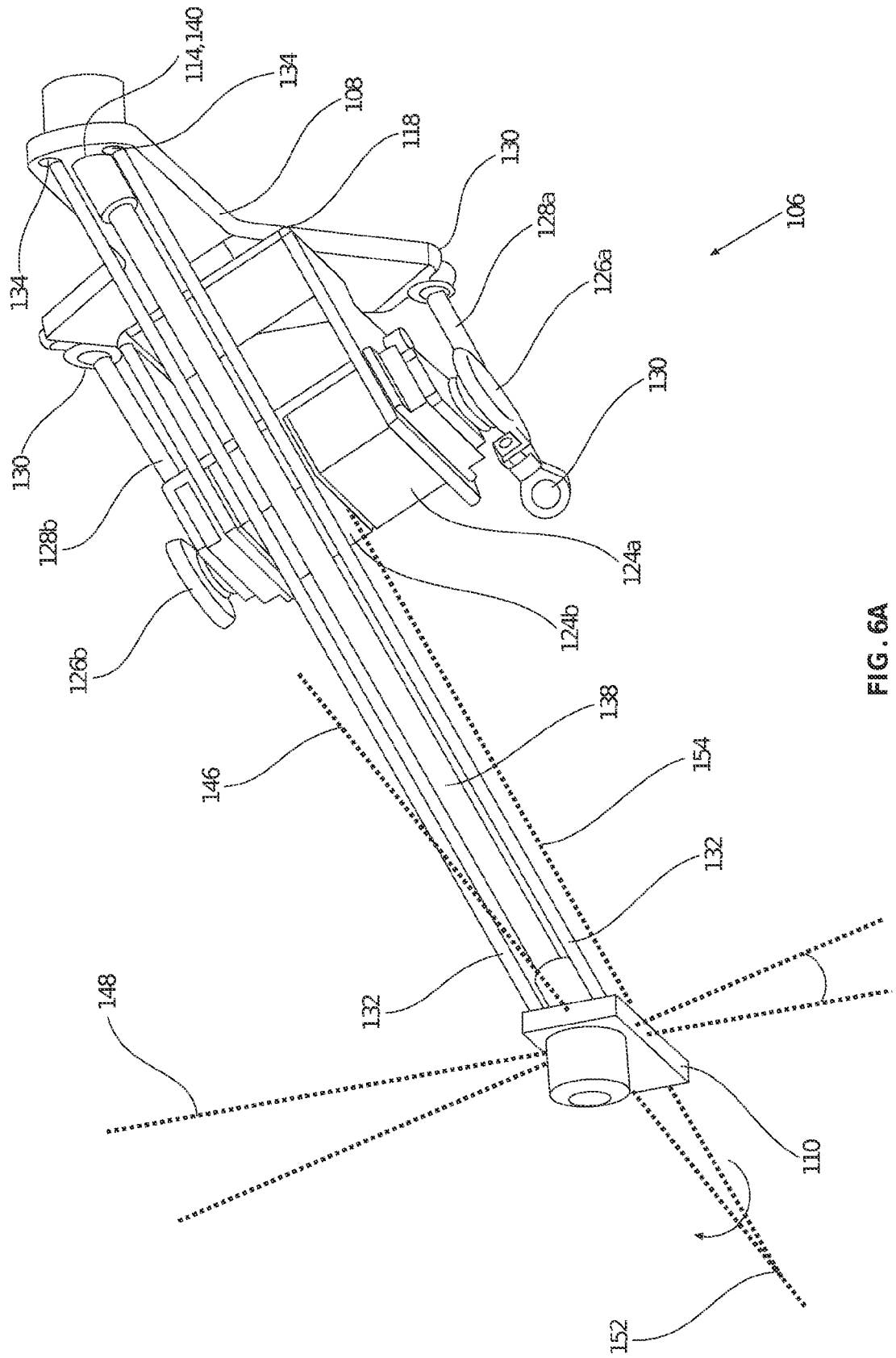
FIG. 6A is a perspective view of the orientation controller of FIG. 5A, in which the controller is rotated around the longitudinal axis.

A change in orientation around the longitudinal axes (roll) is schematically depicted in FIGS. 6A, 6B and 6C. Orientation controller 106 starts from a rest position, as depicted in FIGS. 5A and 5B, as well as schematically from the direction of longitudinal axes 116 and 146 in FIG. 6B.

As depicted in FIGS. 6A and 6C, tilt motors 124 are set to rotate respective tilt wheels 126 in opposite directions, so that tilt arms 128 are moved in opposite directions so that orientation control linker 108 is rotated around longitudinal axis 116. The rotation of orientation control linker 108 is translated to rotation of orientation reception linker 110 around longitudinal axis 146 by orientation transmission rods 132. Through connecting arm 156, the rotation of orientation control linker 108 leads to rotation of mechanical arm 50 and gripper 40 around stationary point 152.

Figure 7A:
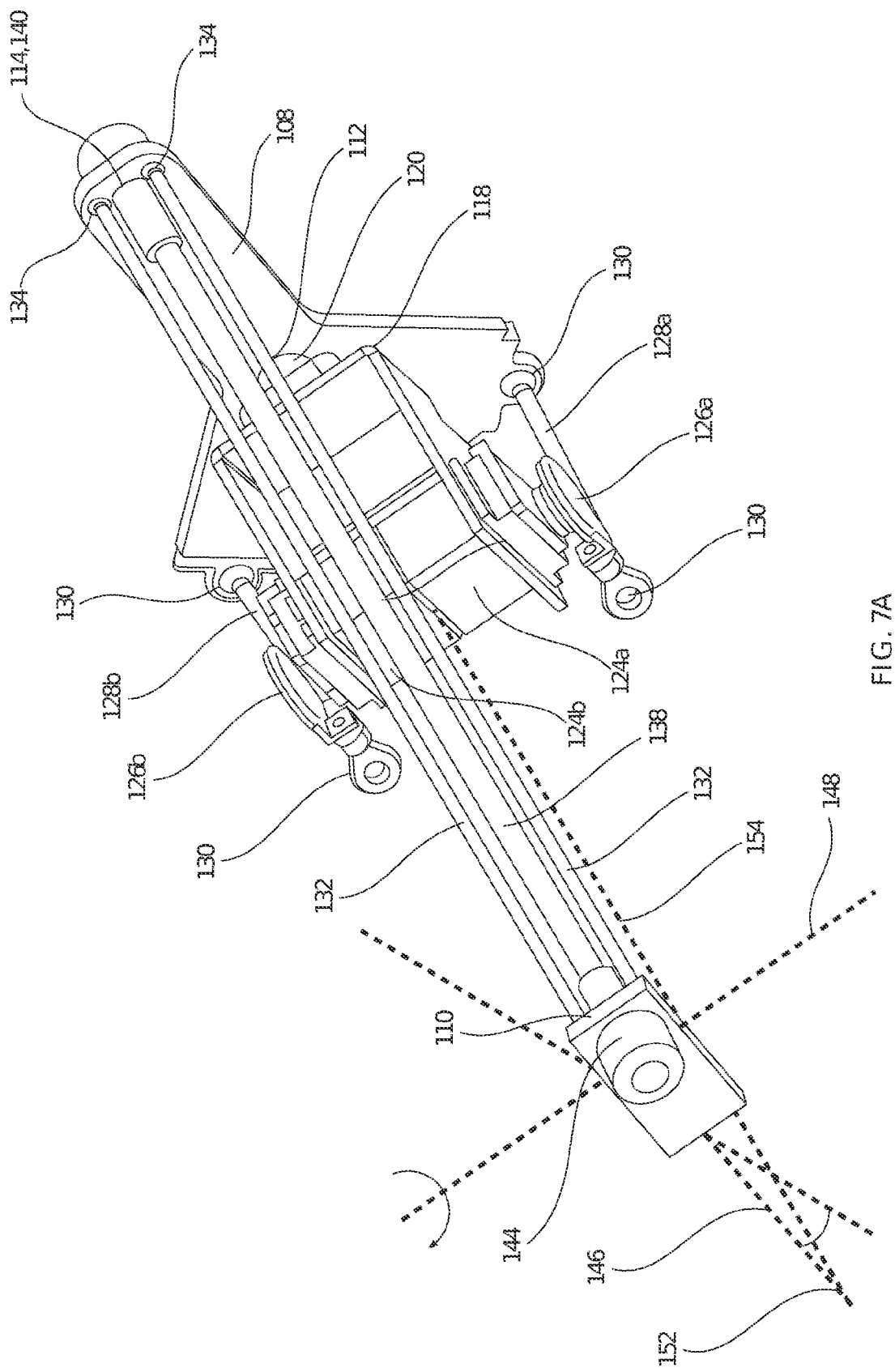
FIG. 7A is a perspective view of the orientation controller of FIG. 5A, in which the controller is rotated around the transverse axis.

A change in orientation around the transverse axes (pitch) is schematically depicted in FIGS. 7A, 7B and 7C. Orientation controller 106 starts from a rest position, as depicted in FIGS. 5A and 5B, as well as schematically from the direction of the transverse axes 122 and 148 in FIG. 7B.

As depicted in FIGS. 7A and 7C, tilt motors 124 are set to rotate respective tilt wheels 126 in the same direction, so that tilt arms 128 are moved in same direction so that orientation control linker 108 is rotated around transverse axis 122. The rotation of orientation control linker 108 is translated to rotation of orientation reception linker 110 around transverse axis 148 by orientation transmission rods 132. Through connecting arm 156, the rotation of orientation control linker 108 leads to rotation of mechanical arm 50 and gripper 40 around stationary point 152.

In the embodiment discussed above, various components are moveably attached through ball joints such as 120 and 130 allowing independent motion in two planes. In other embodiments, any type of joint providing the desired freedom of motion may be used.

In the embodiment discussed above, support rod 138 is collinear with orientation transmission vertical axis 150 providing structural support and mechanical stability to orientation controller 106. In some embodiments, an orientation controller is devoid of a centrally located support rod.

In the embodiment discussed above, there are three orientation transmission rods 132. In some embodiments, an orientation controller is provided with more than three orientation transmission rods, for example in some embodiments, four, five, six or even more orientation support rods.

In the embodiment discussed above, proximal ends 134 of orientation transmission rods 132 are arranged equidistant and symmetrically from orientation transmission point 114, describing a closed curve that is an isosceles triangle. In some embodiments, the orientation transmission point is not equidistant from the different proximal ends of the orientation transmission rods. In some embodiments, the proximal ends of orientation transmission rods are arranged in a different manner having a different shaped closed curve. For example, when there are three transmission rods, the closed curve may be some other triangle, for example an equilateral triangle or a right triangle. For example, when there are four transmission rods, the closed curve may be, for example, a square, a rectangle, a trapeze, a kite, a diamond, or a parallelogram.

In the embodiment discussed above, orientation control linker 108 is a substantially planar object that is collinear with longitudinal axis 116. In some embodiments, an orientation control linker is of a different shape, for example curved or bent.

A challenge known in the art of orienting end effectors is that a stationary point must be well-defined. For example, in the art of keyhole surgery it is desired that an end effector move inside an entry point into the body of a subject, for example defined by a surgical port or incision without pushing against or distending the boundaries of the entry point. As discussed above, in some embodiments, the stationary point of both parallelogram linkages of the orientation controller as described herein coincide and are well defined. Typically, such a stationary point can be positioned at the entry point, so any motion of the end effector caused by the orientation controller is inside the entry point and does not substantially push against or distend the boundaries of the entry point. For example, as discussed above, the stationary points of both parallelogram linkages are located above elbow joint 52 of mechanical arm 50, allowing a change of orientation using an orientation controller such as 106 as well as bending at elbow joint 52 as described above without substantially affecting the entry point.

A challenge known in the art of orienting end effectors is that the space above the area of interest is cluttered with many moving components. For example, in the art of keyhole surgery it is necessary to place many end effectors in the body of a subject so that the volume above the subject is cluttered and inaccessible. In some embodiments, an orientation controller as described herein allows reduction of the clutter from above a subject, by moving bulky components that otherwise would be found above the subject further away by the length between the pivot point and the orientation transmission point as well as by the height of the orientation transmission rods, as well as due to the modest dimensions of the connecting arm, the orientation transmission rods and the orientation reception linker.

In FIG. 8, the use of the teachings herein in the field of keyhole surgery are schematically depicted. In FIG. 8, two orientation controllers 106a and 106b are depicted simultaneously arrayed around a single subject 160 (depicted in cross section) each orientation controller 106 bearing a respective tool 162 with end effector that passes into subject 160 through a respective surgical port 170 where a respective stationary point 152 is located in the center of a respective surgical port 170.

Orientation controller 106a is positioned so that in a rest position (as depicted) a vertical axis 154a is perpendicular to subject 160.

Orientation controller 106b is positioned so that in a rest position (as depicted) a vertical axis 154b is at angle relative relative to subject 160.

In some (non-depicted) embodiments, the dimensions of different orientation controllers are different, for example two different orientation controllers have orientation transmission rods 132 of different lengths or a different distance between a pivot point 112 and a respective orientation transmission point 114, allowing "stacking" and "interleaving" of components of two different orientation controllers.

The modest dimensions of the components in proximity to subject 160 and/or different dimensions of orientation controllers 106 and/or the positioning of orientation controllers 106 at different angles relative to a subject allows many tools 162 secured to an orientation controller 106 to simultaneously be in proximity of subject 160.

Surgical Port

Figure 9:
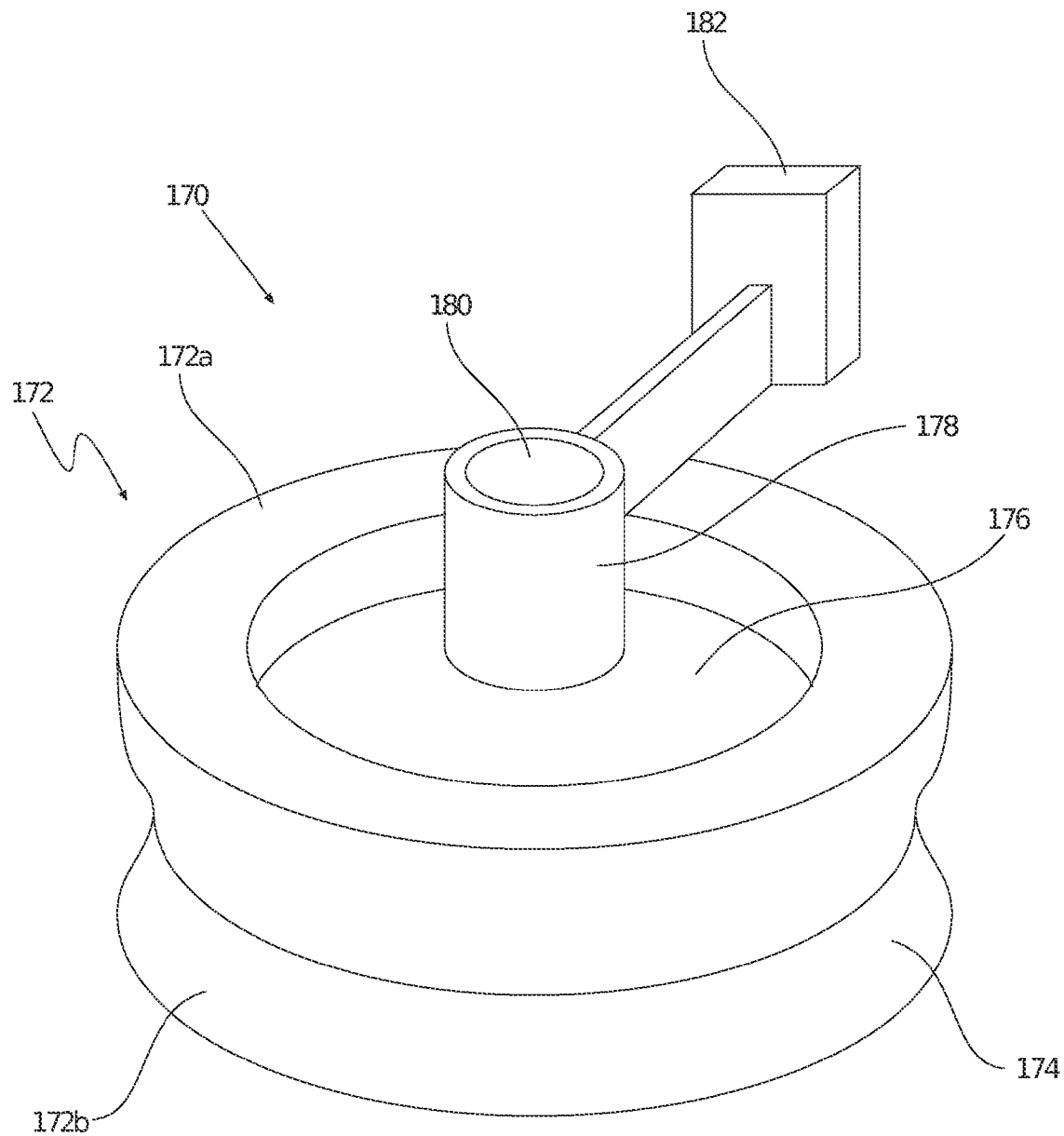
FIG. 9 is a perspective view of an embodiment of a surgical port for performing keyhole surgery as described herein.

An aspect of the invention is a surgical port suitable for use with an orientation controller as described herein. An embodiment of such a surgical port, surgical port 170, is schematically depicted in FIG. 9.

Surgical port 170 comprises a ring-shaped body section 172 made up of an upper body section 172a and lower body section 172b with an outer ring-shaped surface 174. The inner surface of body section 172 comprises a spherical housing to rotatably hold ball member 176. Ball member 176 includes tube 178 defining a passage 180 through ball member 176. Inside passage 180 is a valve (e.g., flaps of elastic material such as silicone rubber). Attached to tube 178 is adaptor 182, configured for attachment to a connecting arm 156 of an orientation controller as described herein.

For use, surgical port 170 is deployed in the usual way in an incision in the body of a subject undergoing keyhole surgery. Outer ring-shaped surface 174 is placed in an incision forming an air-tight seal. Adaptor 182 is connected to a connecting arm 156 of an orientation controller so that the stationary point of the orientation controller coincides with the center of ball member 176. Subsequently, the orientation of passage 180, as well as tools and end effectors passing through passage 180, can be controlled substantially as described above with the use of the orientation controller attached to adaptor 182 that rotates ball member 176 inside the spherical housing defined by body section 172.

Surgical port 170 includes an adaptor 182 for attachment to an orientation controller as described herein. In some embodiments, a surgical port as described herein is devoid of such an adaptor. Instead, a tool or an end effector is directly attached to an orientation controller and then passed into the body of the subject through a passage 180 of the surgical port where the stationary point coincides with the center of a ball member 176 of the surgical port. In such embodiments, the ball member 176 is rotated inside the spherical housing defined by the body section 172 by the force applied by the end effector.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although selected embodiments of the invention has/have been shown and described, it is to be understood that the invention is not limited to the described embodiments. Instead, it is to be appreciated that changes may be made to this/these embodiments without departing from the principles and spirit of the invention, the scope of which is defined by the claims and the equivalents thereof.

Citation or identification of any reference in this application shall not be construed as an admission that such reference is available as prior art to the invention.

Section headings are used herein to ease understanding of the specification and should not be construed as necessarily limiting.

The invention claimed is:

1. A mechanical gripper comprising: an articulated mechanism comprising:
    a segment coupled to a joint; and
    an elongated component coupled to said segment, where applying a pulling force to said elongated component rotates said segment around said joint elastically deforming by bending said elongated component;
    wherein said elastically deforming by bending generates an elongated component elastic force sufficient to rotate said segment, in an opposite direction, in absence of said pulling force.

2. The mechanical gripper of claim 1, wherein said elastic force is a lateral elastic force.

3. The mechanical gripper of claim 1, wherein said elongated component retains a length of said elongated component under said pulling force and in absence of said pulling force.

4. The mechanical gripper of claim 1, wherein the articulated mechanism is used to perform keyhole surgery.

5. The mechanical gripper of claim 1, wherein said pulling force is an axial stretching force.

6. The mechanical gripper of claim 1, wherein said segment comprises an axial void and said elongated component is secured to said segment inside said axial void.

7. The mechanical gripper of claim 6, wherein said elongated component is secured to said segment off a central axis of said segment.

8. The mechanical gripper of claim 7, wherein said elongated component is secured to a part of said segment and coupled to a different part of said segment.

9. The mechanical gripper of claim 1, comprising:
    a second segment coupled to said elongated component and coupled at said joint to said segment.

10. The mechanical gripper of claim 9, wherein said elongated component rotates said second segment around a second joint;
    wherein said elastic force is sufficient to rotate said segment in an opposite direction and said second segment in absence of said pulling force.

11. The mechanical gripper of claim 10, comprising:
    a third segment coupled to a palm at a third joint, coupled to said elongated component and coupled at said second joint to said second segment;
    wherein said elastic force is sufficient to rotate said segment and said second segment in a second direction in absence of said pulling force.

12. The mechanical gripper of claim 9, comprising:
    a second elongated component secured to said second segment, where applying a pulling force to said second elongated component rotates said second segment around a second joint elastically deforming said second elongated component;
    wherein said elastic deformation generates an elongated component elastic force sufficient to rotate said second segment in an opposite direction in absence of said pulling force.

13. The mechanical gripper of claim 1, wherein said elongated component is in the form of a wire.

14. The mechanical gripper of claim 1, wherein said elongated component comprises superelastic material.

15. The mechanical gripper of claim 14, wherein said superelastic material is nitinol.

16. The mechanical gripper of claim 1, wherein said segment is less than 22 mm wide.

17. The mechanical gripper, comprising a plurality of articulated mechanisms according to claim 1, said mechanisms arranged so that said rotation of segments brings said rotated segments towards each other.

18. The mechanical gripper of claim 17, comprising:
    a palm to which said plurality of articulated mechanisms are pivotally connected by said joints.

19. The mechanical gripper of claim 17, wherein said rotation of said segments brings distal ends of said segments towards each other.

20. A method of movement of a mechanical gripper comprising an articulated mechanism, the method comprising:
    pulling and elastically deforming by bending an elongated component coupled to a segment, where pulling rotates said segment; and
    releasing and elastically relaxing said elongated component to rotate said segment in an opposite direction.

21. The method of claim 20, wherein said pulling rotates a second segment, coupled to said elongated component and said segment, curving a long axis of the articulated mechanism; and
    wherein said releasing comprises elastically relaxing said elongated component to rotate said second segment in an opposite direction.

22. The method of claim 21, wherein said pulling comprises pulling and elastically deforming a second elongated component coupled to said second segment; and
    releasing comprises releasing and elastically relaxing said second elongated component to rotate said second segment in an opposite direction.

23. The method of claim 20,
wherein said pulling rotates said segment towards a second segment;
wherein said releasing rotates said segment away from said second segment;
the method comprising:
pulling and elastically deforming a second elongated component coupled to said second segment, where pulling said second segment rotates said second segment towards said segment;
releasing and elastically relaxing said second elongated component to rotate said second segment away from said segment.

24. The method of claim 20, wherein said elastic force is a lateral elastic force.

* * * * *